(12) United States Patent
Andrean et al.

(10) Patent No.: US 7,204,857 B1
(45) Date of Patent: Apr. 17, 2007

(54) DYEING METHOD USING A SPECIFIC ACTIVE METHYLENE COMPOUND AND A COMPOUND SELECTED AMONG A SPECIFIC ALDEHYDE, A SPECIFIC KETONE, A QUINONE AND A DI-IMINO-ISOINDOLINE OR 3-AMINO-ISOINDOLONE DERIVATIVE

(75) Inventors: Hervé Andrean, Paris (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/622,665

(22) PCT Filed: Dec. 22, 1999

(86) PCT No.: PCT/FR99/03245

§ 371 (c)(1),
(2), (4) Date: Oct. 20, 2000

(87) PCT Pub. No.: WO00/38638

PCT Pub. Date: Jul. 6, 2000

(51) Int. Cl.
*A61K 7/13* (2006.01)

(52) U.S. Cl. .................. 8/405; 8/406; 8/409; 8/423; 8/567; 8/565; 8/568; 8/569; 8/571; 8/572; 8/573; 8/574; 8/575; 8/577; 8/578; 8/602; 8/607; 8/608; 548/300; 560/231; 568/420; 549/1; 546/249

(58) Field of Classification Search .............. 8/405, 8/409, 423, 565, 568, 569, 570, 571, 572, 8/573, 574, 575, 576, 577, 578, 579, 602, 8/607, 608, 567; 548/300; 560/231; 546/249; 568/420; 549/1

See application file for complete search history.

(56) References Cited

U.S. PATENT DOCUMENTS

| | | | | |
|---|---|---|---|---|
| 3,634,013 A | * | 1/1972 | Maul et al. | 8/409 |
| 4,010,872 A | * | 3/1977 | Lozano et al. | 222/94 |
| 4,196,145 A | * | 4/1980 | Halasz et al. | 564/305 |
| 5,034,014 A | * | 7/1991 | Wenke | 8/408 |
| 5,595,197 A | * | 1/1997 | Samain et al. | 132/208 |
| 5,616,150 A | | 4/1997 | Moeller et al. | 8/405 |
| 5,628,799 A | * | 5/1997 | Wenke et al. | 8/407 |
| 5,980,585 A | * | 11/1999 | Terranova et al. | 8/409 |
| 6,106,578 A | * | 8/2000 | Jones | 8/406 |

FOREIGN PATENT DOCUMENTS

| | | |
|---|---|---|
| DE | 43 14 317 | 11/1994 |
| EP | 0 847 749 | 6/1998 |
| EP | 0 873 745 | 10/1998 |

OTHER PUBLICATIONS

Jerry March, "Advanced Organic Chemistry, Reactions, Mechanisms, and Structure", Fourth Edition, pp. 279, 741, and 795.
English language Derwent Abstract of EP 0 847 749, Jun. 17, 1998.
English language Derwent Abstract of EP 0 873 745, Oct. 28, 1998.

* cited by examiner

*Primary Examiner*—Eisa Elhilo
(74) *Attorney, Agent, or Firm*—Finnegan, Henderson, Farabow, Garrett & Dunner L.L.P.

(57) ABSTRACT

The present invention relates to the use, for dyeing keratin fibres, of at least one specific compound containing active methylene and of at least one compound chosen from an aldehyde, a ketone, a quinone and a diiminoisoindoline or 3-aminoisoindolone derivative, which makes it possible to obtain, by reaction without an oxidizing agent, a coloration of the said keratin fibres.

53 Claims, No Drawings

DYEING METHOD USING A SPECIFIC ACTIVE METHYLENE COMPOUND AND A COMPOUND SELECTED AMONG A SPECIFIC ALDEHYDE, A SPECIFIC KETONE, A QUINONE AND A DI-IMINO-ISOINDOLINE OR 3-AMINO-ISOINDOLONE DERIVATIVE

The present invention relates to the use, for dyeing keratin fibres, of at least one specific compound containing active methylene and of at least one compound chosen from an aldehyde, a ketone, a quinone and a diiminoisoindoline or 3-aminoisoindolone derivative, to dye compositions comprising a combination of these compounds, to dyeing processes using the said compounds and to a multi-compartment device containing these compounds.

It is known practice, for the dyeing of keratin fibres, and in particular of human keratin fibres such as the hair, to use direct dyes or coloured substances which give the fibres a temporary or semi-permanent coloration, of low dyeing power, which is generally removed by washing or perspiration. The range of shades obtained by these direct processes are generally limited. It is also known practice to use oxidation dyes (oxidation bases and couplers), which are compounds which are initially colourless or weakly coloured and which, under the action of an oxidizing agent, generate coloured compounds by a process of oxidative condensation. Compared with direct colorations, oxidative colorations are permanent, powerful and withstand external agents (light, bad weather, washing, perspiration and rubbing). Nevertheless, the use of the oxidizing agent can harm the keratin fibres and make the processes for carrying out the oxidative dyeing operations relatively complex.

The Applicant has just discovered a novel dyeing process, which does not involve a process of oxidative development of dyes, and which gives a wide range of shades.

The compounds used by the Applicant are small molecules which can penetrate into keratin easily. The Applicant has found, surprisingly, that these compounds can then condense to form chromophores or dyes, bulkier molecules which remain trapped inside the keratin.

The Applicant has thus found that the dyes obtained withstand shampooing and perspiration and are stable with respect to light, bad weather and chemical agents. The Applicant has, in a way, discovered a novel dyeing process which has the advantages of so-called oxidation dyeing without exhibiting its drawbacks, since no oxidizing agent is used.

One subject of the present invention is thus the use, for dyeing keratin fibres, of a specific compound containing active methylene and of a compound chosen from a specific aldehyde, a specific ketone, a quinone and a diiminoisoindoline or 3-aminoisoindolone derivative.

Another subject of the invention relates to dye compositions comprising these compounds.

A subject of the present invention is also a process for dyeing keratin fibres, which consists in applying a specific compound containing active methylene and a compound chosen from a specific aldehyde, a specific ketone, a quinone and a diiminoisoindoline or 3-aminoisoindolone derivative to the fibres, either simultaneously, in the form of a mixture prepared at the time of use, or successively.

Another subject of the invention also consists of a dyeing agent for carrying out the process of the invention.

Other subjects of the invention will become apparent in the light of the description.

The main subject of the present invention is thus the use, for dyeing keratin fibres, in particular human keratin fibres such as the hair, of at least one specific compound containing active methylene and of at least one compound chosen from an aldehyde, a ketone, a quinone and a diiminoisoindoline or 3-aminoisoindolone derivative, in order to obtain, by reaction without an oxidizing agent, a coloration of the said keratin fibres.

In the context of the present invention, a compound containing active methylene is defined as a methylene group substituted with two groups with an electron-withdrawing effect or mesomeric effect. Such compounds are described in particular in Advanced Organic Chemistry Jerry March, 4th edition, Wiley Intersciences, pages 279, 741 and 795.

The compounds containing active methylene of the present invention are chosen more particularly from:

1) the compounds of formula (I) below:

(I)

in which:

$R_1$ denotes a group —COR or —COOR with R denoting a hydrogen atom or an alkyl group, $R_1$ denotes the groups denoted by $R_1$, a nitrile group, a substituted or unsubstituted aryl or alkylaryl group, or a substituted or unsubstituted heterocycle;

2) the compounds of formula (II) below:

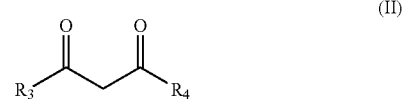
(II)

(II)

in which:

$R_3$ denotes the groups denoted by $R_2$ $R_4$ denotes a substituted or unsubstituted alkyl group, an acetyloxy group, a cycloalkyl group, a substituted or unsubstituted alkylaryl group, an aralkyl group, a substituted or unsubstituted aryl group, a substituted or unsubstituted aminoaryl group or a substituted or unsubstituted heterocycle;

3) the compounds of formula (III) below:

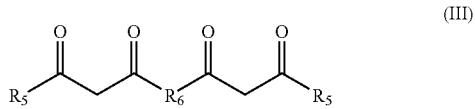
(III)

in which:

$R^5$ denotes the groups denoted by $R_2$ $R^6$ denotes a substituted or unsubstituted aryl or aralkyl group, a substituted or unsubstituted aminoaryl group or a substituted or unsubstituted heterocycle;

4) the pyrazole derivatives (i) of formulae (IV) and (V) below:

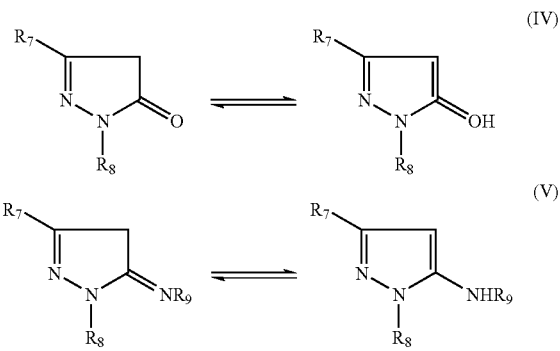

in which:

R$_7$ and R$_8$, which may be identical or different, denote the groups denoted by R$_4$, R$_9$ denotes a hydrogen atom or a substituted or unsubstituted alkyl group;

and (ii) formed by two pyrazole rings of formula (IV) or (V) linked by R$_7$ or R$_8$;

5) the barbituric acid derivatives (i) of formula (VI) below:

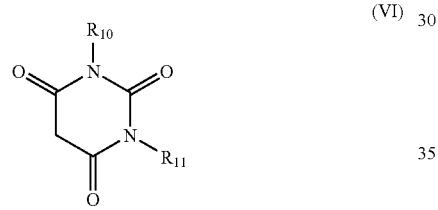

in which:

R$_{10}$ and R$_{11}$, which may be identical or different, denote a substituted or unsubstituted alkyl group, an alkenyl group, a cycloalkyl group, an alkylaryl group or a substituted or unsubstituted aryl group, and (ii) the compounds formed by two rings of formula (VI) linked by R$_{10}$ or R$_{11}$;

6) the pyridine derivatives of formula (VII):

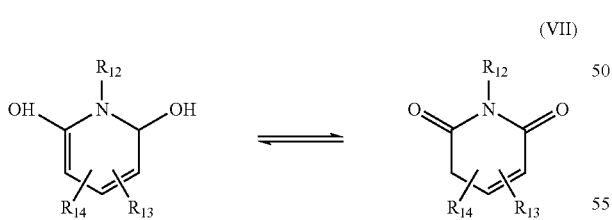

in which:

R$_{12}$ denotes a substituted or unsubstituted alkyl group or a substituted or unsubstituted aryl group;

R$_{13}$ denotes a hydrogen atom, a substituted or unsubstituted alkyl group or a substituted or unsubstituted aryl group;

R$_{14}$ denotes a hydrogen atom, a nitrile group, a substituted or unsubstituted alkyl group, or a group COOR, R denoting a hydrogen atom or a substituted or unsubstituted alkyl group;

7) the derivatives of formula (VIII) below;

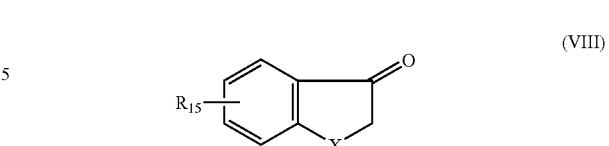

in which:

X denotes an oxygen, sulphur or nitrogen atom or a group NR', R' denoting an alkyl group, R$_{15}$ denotes a hydrogen, chlorine or bromine atom or a hydroxyl, nitro, alkyl, alkoxy, carboxamide, sulphonamide or nitrile group;

8) the derivatives of formulae (IX) and (X) below;

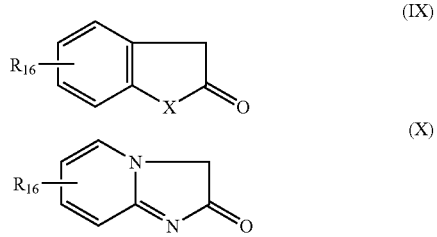

in which:

X denotes an oxygen, sulphur or nitrogen atom or a group NR', R' denoting an alkyl group, R$_{14}$ denotes the atoms and groups denoted by R$_{15}$;

9) the derivatives of formula (XI) below:

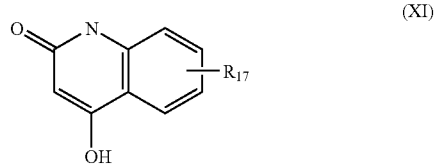

in which:

R$_{17}$ denotes a hydrogen atom, a hydroxyl group, a substituted or unsubstituted alkyl group or a substituted or unsubstituted aryl or alkylaryl group;

10) the indanedione derivatives of formula (XII) below:

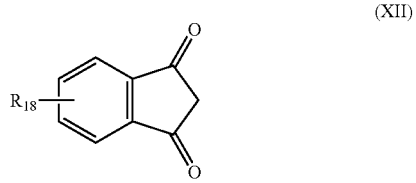

in which:

R$_{18}$ denotes a hydrogen, chlorine or bromine atom or a nitro, alkyl, alkoxy, carboxamide, sulphonamide or nitrile group;

11) the derivatives of formula (XIII) below:

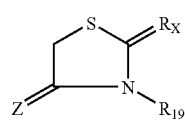
(XIII)

in which:

Z denotes O or NR with R=H or alkyl $R_x$ denotes a sulphur atom or NR, R denoting a hydrogen atom or an alkyl group;

$R_{19}$, denotes a hydrogen atom or an alkyl, alkoxy, nitro or nitrile group;

12) the dioxopyrazole derivatives of formula (XIV) below:

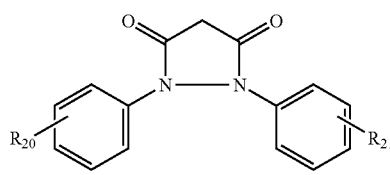
(XIV)

in which:

$R_{20}$ and $R_{21}$, which may be identical or different, denote a hydrogen atom or an alkyl, alkoxy, nitro or nitrile group;

13) the 5-oxoimidazole derivatives of formula (XV) below:

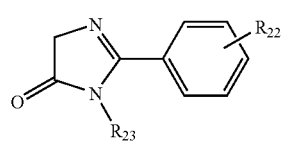
(XV)

in which:

$R_{22}$ denotes a hydrogen atom or an alkyl group $R_{23}$ denotes a hydrogen atom or an alkyl, alkoxy, nitro or nitrile group;

14) the dehydrobutyrolactone derivatives of formula (XVI) below:

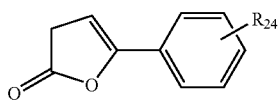
(XVI)

in which:

$R_{24}$ denotes a hydrogen atom or an alkyl, alkoxy, nitro or nitrile group;

15) the compounds of formula (XVII) below:

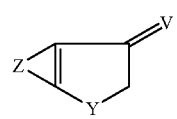
(XVII)

in which:

Z forms an aromatic ring

V denotes an oxygen atom or a group

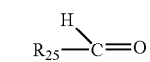

in which A or E denotes a substituent having a Hammet constant of between 0.4 and 2.0 or substituents for which the sum of the Hammet constants is between 0.4 and 2.0

Y denotes Co, O, S or $NR_1$ when V is other than an oxygen atom, or denotes CS, C=$NR_2$, SO or $SO_2$ with $R_1$ or $R_2$ denoting a hydrogen atom or an alkyl radical;

and from the cosmetically acceptable salts of the compounds defined above.

They are used in combination with at least one aldehyde corresponding to formula (XVIII) below:

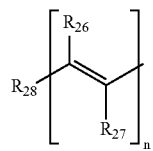
(XVIII)

in which:

$R_{25}$ denotes a group of formula (XVIII A) below:

(XVIII A)

in which $R_{26}$ and $R_{27}$, which may be identical or different, denote a hydrogen atom or an alkyl, mono- or polyhydroxyalkyl, alkylhydroxyalkyl, alkoxy, —$CF_3$ or —$OCF_1$ group, $R_{24}$ and $R_{27}$ can also form, together with the atoms to which they are attached, a 5- or 6-membered heterocyclic or aryl ring, the said rings possibly being substituted or unsubstituted;

n denotes an integer from 0 to 3, $R_{28}$ denotes the substituents denoted by $R_{26}$, a substituted or unsubstituted aryl or alkylaryl group or a substituted or unsubstituted 5- or 6-membered heterocyclic group, or with the cosmetically acceptable salts of these compounds;

a ketone corresponding to formulae (XIX) or (XX) below:

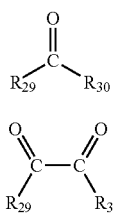

in which:

$R_{29}$ denotes the substituents denoted by $R_{25}$ $R_{30}$ denotes an alkyl, mono- or polyhydroxyalkyl, or hydroxyalkyl group or a substituted or unsubstituted aryl, alkylaryl or 5- or 6-membered heterocyclic group, $R_{29}$ and $R_{30}$ can also form, together with the atoms to which they are attached, a 5- or 6-membered aryl ring or a heterocyclic ring comprising hetero atoms such as N or S, it being possible for the said ring itself to be attached to a 5- or 6-membered aryl ring or to a heterocycle comprising hetero atoms such as N or S, the said rings possibly being substituted or unsubstituted, or with the cosmetically acceptable salts of these compounds, a quinone and a diiminoisoindoline or 3-aminoisoindolone derivative, making it possible to obtain, by reaction without an oxidizing agent, a coloration of the said keratin fibres.

Among the compound of formulae (I), (II) and (III) which may be mentioned in particular are malonic acid and its esters and acetoacetic acid and its derivatives.

The compounds of formula (IV) may be, in particular, the following; pyrazolone(5), 3-methylpyrazolone(5), 1-phenyl-3-methylpyrazolone(5), 1-(b-cyanethyl)-3-methylpyrazolone(5), 1,3-dimethylpyrazolone(5), 1-(b-acetoxyethyl)-3-methylpyrazolone(5), 1-(o-chlorophenyl)-3-methylpyrazolone(5), 1-phenyl-3-carbomethoxypyrazolone(5), 1-(3-aminophenylpyrazolone(5)-1-(4-aminophenyl)pyrazolone(5), 3-methylpyrazolone(5)-1-carboxamide, 1-phenylpyrazolone(5)-3-carboxamide, aminopyrazole, 1-phenyl-5-aminopyrazole, 1-benzyl-5-aminopyrazole, 1-cyclohexyl-5-aminopyrazole, 1-ethyl-3-methyl-5-aminopyrazole, 1-benzyl-3-phenyl-5-aminopyrazole, 1-isopentyl-5-aminopyrazole, 1-furfuryl-5-aminopyrazole, 2-methyl-4H-pyrazolo(5)-[2,3-a]-benzimidazole, [1-(3-thiacyclopentyl)-3-methylpyrazolone(5) S-dioxide] and 2-methyl-1H-3,3a, 8-triazacyclopenta [a] indene.

The barbituric acid derivatives of formula (VI) can be chosen from di-n-butyl-, diisobutyl-, di-N-amyl-, diisoamyl-, di-n-hexyl-, dibenzyl-, di-β-phenylethyl-, dicyclohexyl-, diphenyl-, di-p-tolyl- and di-p-methoxybenzyl-barbituric acids; N-methyl-N'-n-butyl-, N-methyl-N'-benzyl-, N-methyl-N'-β-phenylethyl-, N-methyl-N'-β-phenylpropyl-, N-methyl-N'-γ-phenylbutyl-, N-methyl-N'-α-isobutyl-γ-phenylpropyl-, N-methyl-N'-cyclohexyl-, N-methyl-N'-phenyl-, N-methyl-N'-p-tolyl- and N-methyl-N'-norbornylmethyl-barbituric acids and the corresponding N-ethyl and N-n-butyl derivatives.

The pyridines and pyridones of formula (VII) may be, for example, 2,6-dihydroxy-3-cyano-4-methylpyridine, those of the cyanopyridone, aminonitropyridone and aminocyanopyridone families and in particular: N-methyl-3-cyano-4-methyl-6-hydroxy-2-pyridone, N-ethyl-3-cyano-4-methyl-6-hydroxy-2-pyridone, N-b-methoxyethyl-3-cyano-4-methyl-6-hydroxy-2-pyridone, 2,6-dihydroxy-3-cyano-4-methylpyridine, N-b-hydroxyethyl-3-cyano-4-methyl-6-hydroxy-2-pyridone, N-butyl-3-cyano-4-methyl-6-hydroxy-2-pyridone and N-phenyl-3-cyano-4-methyl-6-hydroxy-2-pyridone.

The derivatives of formula (VIII) can be chosen in particular from 6-hydroxybenzofuran-(2H)-one and benzofuran-(2H)-one.

The derivatives of formula (IX) may be, for example:

1,3-dihydroindol-2-one
3H-benzofuran-2-one
1-methyl-1,3-dihydroindol-2-one
5-methoxy-3H-benzofuran-2-one
5-nitro-1,3-dihydroindol-2-one
1-methyl-5-nitro-1,3-dihydroindol-2-one
6-methoxy-1,3-dihydroindol-2-one
5-chloro-1,3-dihydroindol-2-one
5,6-difluoro-1,3-dihydroindol-2-one
6-hydroxy-5-methoxy-1,3-dihydroindol-2-one
5,6-dimethoxy-1,3-dihydroindol-2-one
6-trifluoromethyl-1,3-dihydroindol-2-one.

Derivatives of formula-(X) may be, for example:

imidazo[1,2-a]pyridin-2-one
6-bromoimidazo[1,2-a]pyridin-2-one.

The derivatives of formula (XI) are preferably chosen from the derivatives for which $R_{17}$ denotes a hydrogen atom, such as, for example, 2,4-dihydroxyquinoline.

The derivatives of formula (XII) correspond in particular to 1'1,3-indanedione.

The derivatives of formula (XIII) are preferably chosen from rhodamine and 4-imino-4,5-dihydrothiazol-2-ylamine.

A derivative of formula (XIV) which may be mentioned is 1,2-diphenyldioxopyrazole.

The derivatives of formula (XV) are chosen in particular from;

2-phenyl-3,5-dihydroimidazol-4-one
3-methyl-2-p-tolyl-3,5-dihydroimidazol-4-one.

A preferred compound of formula (XVI) which may be mentioned is phenyldihydrobutyrolactone.

Preferred compounds of formula (XVII) which may be mentioned are:

1,1-dioxo-1,2-dihydro-11,6-benzo[b]thiophen-3-one and 2-(1,1-dioxo-1,2-dihydro-11,6-benzo[b]thiophen-3-ylidene) malononitrile.

The quinone can correspond to formulae (XXI) and (XXII) below;

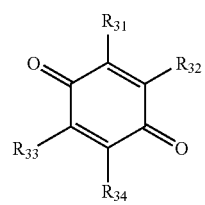

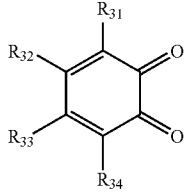

(XXII)

in which:

$R_{31}$, denotes a hydrogen or halogen atom or a sulphonic or alkoxy group, $R_{32}$, $R_{33}$ and $R_{34}$, which may be identical or different, denote a hydrogen or halogen atom, a hydroxyl, alkyl, mono- or polyhydroxyalkyl, alkylhydroxyalkyl, alkyl-sulphonyl, carboxyalkyl, aminoalkyl, alkylaminoalkyl, (dihydroxy)alkylaminoalkyl or alkyl-NR'R" group (with R' and R" denoting alkyl or possibly forming, together with the nitrogen atom to which they are attached, an aryl ring or a 5- or 6-membered heterocycle), an aryl group or an amino group which can be substituted with an alkyl or a hydroxyalkyl, $R_{31}$ and $R_{32}$, $R_{31}$ and $R_{33}$, or $R_{33}$, and $R_{34}$ can form, together with the atoms to which they are attached, a substituted or unsubstituted aryl ring or 5- or 6-membered heterocycle;

or to the cosmetically acceptable salts of these compounds.

The diiminoisoindoline or 3-aminoisoindolone derivatives can be those corresponding to formula (XXIII) below:

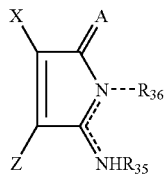

(XXIII)

in which:

$R_{35}$ and $R_{34}$, which may be identical or different, denote a hydrogen atom, an alkyl, mono- or polyhydroxyalkyl, alkylhydroxyalkyl, aminoalkyl, alkylaminoalkyl or (dihydroxy) alkylaminoalkyl group or an alkyl-NR'R" group, with R' and R" denoting alkyl or possibly forming, together with the nitrogen atom to which they are attached, an aryl ring or a 5- or 6-membered heterocycle, A denotes an oxygen atom or NH, X and Z together form a substituted or unsubstituted aryl ring or a 5- or 6-membered heterocycle; or to the cosmetically acceptable salts of these compounds.

Among the preferred compounds of formula (XVIII) which may be mentioned in particular are benzaldehyde, 2,3,4-monohydroxybenzaldehydes, 2,3,4-monomethoxybenzaldehydes, 2,3,4-monomethylbenzaldehydes, (2,3)-, (2,4)-, (2,5)-, (2,6)- and (3,5)-dihydroxybenzaldehydes, (2,3)-, (2,4)-, (2,5)-, (2,6)- and (3,5)-dimethoxybenzaldehydes, vanillin, iso-vanillin, syringaldehyde, ortho-, iso- and terephthalaldehyde, (2,3)-, (2,4)-, (2,5)-, (2,6)- and (3,5)-dimethylbenzaldehydes, 4-isopropylbenzaldehyde, 4-dimethylaminobenzaldehyde, 4-diethylaminobenzaldehyde, piperonal, (2,6)- and (3,5)-dimethyl-4-hydroxybenzaldehyde, 2,3,4-mononitrobenzaldehydes, 2-hydroxy-3-methoxybenzaldehyde, 2-hydroxy-4-methoxy-benzaldehyde, 2-hydroxy-5-methoxy-benzaldehyde, 2-hydroxy-6-methoxybenzaldehyde, 4-methylthiobenzaldehyde, (2,3,4)-, (2,4,6)-, (3,4,5)- and (2,4,5)-tri-hydroxybenzaldehydes, methyl 2-, 3- and 4-formyl-benzoates, 2,3,4-mono(2-hydroxyethoxy)benzaldehydes, 4-nitro-3-hydroxybenzaldehyde, 3-nitro-4-hydroxybenzaldehyde, 2-nitro-4-hydroxybenzaldehyde, 3-nitro-2-hydroxybenzaldehyde, 2,3,4-monotrifluorobenz-aldehydes, 2,3-dihydroxy-4-methoxybenzaldehyde, 3,4-dihydroxy-5-methoxybenzaldehyde, 3,5-dihydroxy4-methoxy-benzaldehyde, 3-methoxy-2-nitrobenzaldehyde, 4-methoxy-2-nitrobenzaldehyde, 2-methoxy-3-nitrobenzaldehyde, 4-methoxy-3-nitrobenzaldehyde, (2,3,4)-, (2,4,6)-, (3,4,5)- and (2,4,5)-trimethoxybenzaldehydes, 5-nitrovanillin, (2,4)- and (2,6)-dinitrobenzaldehydes, pentamethylbenzaldehyde, 4-methylsulphonylbenzaldehyde, 2,3,4-monoformyl-phenoxyacetic acids, 4-diethylaminosalicylaldehyde, 4-(3-dimethylaminopropoxy)benzaldehyde, 2,3-dihydrobenzo(b)furan-5-carboxaldehyde, 1- and 2-naphthaldehyde, 6- and 5-carboxaldehyde-1,4-benzodioxane, 2,4-monohydroxy-1-naphthaldehydes, 1-monohydroxy-2-naphthaldehyde, 1-(4-formylphenyl)imidazole, 4-pyrrolidinolbenzaldehyde, 2,4-monomethoxy-1-naphthaldehydes, 2,3-dimethylchroman-6-carboxaldehyde, 2,3,6,7-tetrahydro-1H,5H-pyrido(3,2,1-IJ)quinoline-9-carbaldehyde, 4-dimethylamino-1-naphthaldehyde, 9-anthraldehyde, 3-nitro-4-pyrrolidinobenzaldehyde, 3-nitro-4-piperidinobenzaldehyde, 3-nitro-4-morpholino-benzaldehyde, pyridine 2,3,4-monocarboxaldehydes, 2,6-pyridinodicarboxaldehyde, 5-formyl-6-methyluracil, pyridoxal, quinoline-2,3,4-monocarboxaldehydes, 8-hydroxyquinoline-2-carboxaldehyde, 2- and 3-furaldehydes, 2- and 3-thienylcarboxaldehydes, 2- and 3-imidazocarboxaldehydes, 2-pyrrolecarboxaldehyde, 5-nitro-2-furaldehyde, 5-(dimethylamino)-2-furaldehyde, 2,5 and 2,3-thiophenedicarboxaldehydes, pyrazole-3-carbaldehyde, 5-nitro-2-thiophenecarboxaldehyde, 5-nitro-3-thiophenecarboxaldehyde, indole-3-carboxaldehyde, N-methyl-indole-3-carboxaldehyde, 2-methylindole-3-carboxaldehyde, 4,5,6,7-monomethyl-indolecarboxaldehyde and 5-formyl-2-furansulphonic acid.

The ketones of formulae (XIX) and (XX) can be chosen from 2,3-indolinedione, 2,3-butanedione, 2,3-pentanedione, (2,3)- and (3,4)-hexanedione, 1-phenyl-1,2-propanedione, benzil, furil, 2,2'-pyridil, nitrobenzil, anisil, 3,3'-dimethoxybenzil, 4,4'-bis-(dimethylamino)benzil, camphoroquinone, cyclohexane-1,2-dione, isatin, N-methylisatin, 4-, 5-, 6- and 7-monomethylisatin, (4,5)-, (4,7)-, (5,7)- and (6,7)dimethylisatin, N-ethylisatin, N-hydroxymethylisatin, 5-, 6- and 7-monomethoxyisatin, 4-, 5-, 6- and 7-monochloroisatin, 4-, 5-, 6- and 7-monobromoisatin, N-isopropylisatin, N-butylisatin, N-propylisatin, 5-nitroisatin, isatin-5-sulphonic acid, 2,4,5-trihydroxypyrimidine, alloxan, 1,3-dimethylhexahydro-2,4,5,6-pyrimidinetetrone, ninhydrin, chinisatin, 1,3-indenedione, squaric acid, croconic acid, 3,4-dimethoxy-3-cyclobutene-1,2-dione, 3- and 4-ethoxy-3-cyclobutene-1,2-dione, 3- and 4-isopropoxy-3-cyclo-butene-1,2-dione, 3,4-di-N-butoxy-3-cyclobutene-1,2-dione, rhodizonic acid, oxindole, N-methyl-2-indolin-one, N-methylnitro-2-indolinone, 6-methoxyoxindole, 5,6-dimethoxyoxindole and 5- and 6-monochlorooxindole.

The preferred quinones of formulae (XXI) and (XXII) are, inter alia, 1,4-naphthoquinone, spinolusin, atromentin, aurentioglyocladin, 2,5-dihydroxy-6-methylbenzoquinone, 2-hydroxy-3-methyl-6-methoxybenzo-quinone, 2,5-dihydroxy-3,6-diphenylbenzoquinone, 2,3-dimethyl-5-hydroxy-6-methoxybenzoquinone, 2,5-di-hydroxy-6-isopropylbenzoquinone, lawsone, juglone, fafioline, naphthazarine, naphthopurpurine, lapachol, plumbagin, chloroplumbagin, naphthopurpurine, lapachol, plumbagin, chloroplumbagin, droserone, shikonine, 2-hydroxy-3-methyl-1,4-naphthoquinone, 3,5-di-hydroxy1,4-naphthoquinone, 2,5-dihydroxy-1,4-naphthoquinone, 2-methoxy-5-hydroxy-1,4-naphthoquinone, 3-methoxy-5-hydroxy-1,4-naphthoquinone, (1,4) and (1,2)-naphthoquinone, 4,5-dimethoxy-1,2-benzoquinone, phenanthrenequinone and (1,2)-naphthoquinone-4-sulphonic acid.

The derivatives of formula (XXIII) are represented in particular by 3-imino-3H-isoindolylamine, 3-imino-4-methyl-3H-isoindolylamine, 3-imino-4-tert-butyl-3H-isoindol-1-ylamine, 3-imino-7-nitro-3H-isoindol-1-ylamine, 3-amino-1-imino-1H-isoindol-4-ol, 3-imino-7-isopropoxy-3H-isoindol-1-ylamine, 3-imino-7-(2,2,2-trifluoroethoxy)-3H-isoindol-1-ylamine, 3-imino-7-ethoxy-3H-isoindol-1-ylamine, 3-imino-7-butoxy-3H-isoindol-1-ylamine, 3-amino-1-imino-1H-isoindol-4-sulphonic acid, 3-imino-7-chloro-3H-isoindol-1-ylamine, 3-imino-5-methyl-3H-isoindol-1-ylamine, 3-imino-5-ethyl-3H-isoindol-1-ylamine, 3-imino-5-tert-butyl-3H-isoindol-1-ylamine, 3-imino-5-amino-3H-isoindol-1-ylamine, N-(1-amino-3-imino-3H-isoindol-5-yl)acetamide, 3-imino-5-nitro-3H-isoindol-1-ylamine, 3-imino-5-fluoro-3H-isoindol-1-ylamine, 3-imino-5-chloro-3H-isoindol-1-ylamine, 3-imino-5-methylsulphanyl-3H-isoindol-1-ylamine, 3-imino-5-methoxy-3H-isoindol-1-yl-amine, 3-imino-5-ethoxy-3H-isoindol-1-ylamine, 3-imino-5-propoxy-3H-isoindol-1-ylamine, 3-imino-5-isopropoxy-3H-isoindol-1-ylamine, 3-imino-5-butoxy-3H-isoindol-1-ylamine, 3-imino-5-isobutoxy-3H-isoindol-1-ylamine, 3-imino-5-tert-butoxy-3H-isoindol1-ylamine, 3-imino-5-(2,2,2-trifluoromethyl)-3H-isoindol-1-ylamine, 3-imino-5-(2,2,2-trifluoroethoxy)-3H-isoindol-1-ylamine, 3-imino-5-methanesulphonyl-3-H-isoindol-1-yl-amine, 3-imino-5,6-dimethyl-3H-isoindol-1-ylamine, 3-imino-5,6-diethyl-3H-isoindol-1-ylamine, 3-imino-5,6-dimethoxy-3H-isoindol-1-ylamine, 3-imino-5,6-diethoxy-3H-isoindol-1-ylamine, 3-imino-5,6-dibutoxy-3H-isoindol-1-ylamine, 3-imino-5,6-bis(trifluoromethyl)-3H-isoindol-1-ylamine, 3-imino-5,6-dichloro-3H-isoindol-1-ylamine, 5,6-bis(ethoxy-methyl) 3-imino-3H-isoindol-1-ylamine, 3-amino-1-imino-1H-isoindole-4,7-diol, 4,7-dichloro-3-imino-3H-isoindol-1-ylamine, 4,5,7-trichloro-3-imino-N6,N6-di-methyl-3H-isoindol-1,G-diamine, 4,5,6,7-tetrachloro-3-imino-3H-isoindol-1-ylamine, 4,5,6,7-tetrafluoro-3-imino-3H-isoindol-1-ylamine, 3-butylimino-3-H-isoindol-1-ylamine, 2-(3-aminoisoindol-1-ylideneamino) ethanol, 3-(3-aminoisoindol-1-ylidenamino)-3-methylpentane-1,5-diol, N-(3-aminoisoindol-1-ylidene)-guanidine, 7-imino-7H-pyrrolo[3,4-b]pyrid-5-ylamine, 7-imino-7H-pyrrolo[3,4-b]pyrazin-5-ylamine, 7-imino-2,3-dimethyl-7H-pyrrolo[3,4-b]pyrazin-5-ylamine, 7-imino-7H-[1,4]dithiino[2,3-c]pyrrol-5-ylamine, 7-imino-2,3-dimethyl-7H-[1,4]dithiino[2,3-c]pyrrol-5-ylamine, 7-imino-2-methyl-2,3-dihydro-7H-[1,4]dithiino[2,3-c]pyrrol-5-ylamine, 7-imino-2,3-dihydro-7H-[1,4]dithiino[2,3-c]pyrrol-5-ylamine, 3-aminoisoindol-1-one, 3-amino-7-methylisoindol-1-one, 3-amino-7-hydroxymethylisoindol-1-one, 3-amino-7-chloroisoindol-1-one, 3-amino-4-chloroisoindol-1-one, 3-amino-1-oxo-1H-isoindol-4-sulphonic acid, 3-amino-4-nitroisoindol-1-one, 3-amino-6-nitroisoindol-1-one, 3-amino-6-methylisoindol-1-one, 3-amino-6-chloro-isoindol-1-one, 3-amino-6-bromo-isoindol-1-one, 3-amino-6-methyl-sulphanyl-isoindol-1-one, 3-amino-6-methoxyisoindol-1-one, 3-amino-5-chloroisoindol-1-one, 3-amino-5-fluoroisoindol1-one, 3-amino-5-methoxyisoindol-1-one, 3-amino-5-nitroisoindol-1-one, ethyl 3-amino-1-oxo-1H-isoindole-5-carboxylate, 3-amino-5,6-dichloroisoindol-1-one, 3-amino-5,6-dibromoisoindol-1-one, 3-amino-4,7-dichloroisoindol-1-one, 3-amino-4,5,7-trichloroisoindol-1-one, 3-amino-4,5,6,7-tetrachloroisoindol-1-one, 3-amino-4,5,7-trichloro-6-methylsulphanylisoindol-1-one, 3-amino-4,5,6,7-tetrabromoisoindol-1-one, 3-amino-4,5,6,7-tetrafluoroisoindol-1-one, 3-methylaminoiso-indol-1-one, 3-ethylaminoisoindol-1-one, 3-propylaminoisoindol-1-one, 3-dimethylaminoisoindol-1-one, 7-ethyl-aminopyrrolo[3,4-b]pyrid-5-one, 7-aminopyrrolo[3,4-b]-pyrid-5-one, 3-aminopyrrolo[3,4-c]pyrid-5-one, 3-amino-6-methylpyrrolo[3,4-c]pyrid-1-one, 5-aminopyrrolo[3,4-b]pyrid-7-one, 7-aminopyrrolo[3,4-b]pyrazin-5-one, 7-amino-2-methylpyrrolo[3,4-b]pyrazin-5-one, 7-amino-2,3-dimethylpyrrolo[3,4-b]pyrazin-5-one, 7-amino-2,3-dihydro[1,4]dithiino[2,3-c]pyrrol-5-one, 3-imino-2-methyl-2,3-dihydroisoindol-1-one, 3-imino-2-ethyl-2,3-dihydroisoindol-1-one, 3-imino-2-propyl-2,3-dihydroisoindol-1-one, 2-hydroxymethyl-3-imino-2,3-dihydroisoindol-1-one, 2-(2-hydroxyethyl)-3-imino-2,3-di-hydroisoindol-1-one, 2-(1-imino-3-oxo-1,3-dihydroisoindol-2-yl)ethanesulphonic acid, 3-(1-imino-3-oxo-1,3-dihydroisoindol-2-yl)propionic acid, 2-(3-hydroxypropyl)-3-imino-2,3-dihydroisoindol-1-one and 5-imino-6-methyl-5,6-dihydropyrrolo[3,4-b]pyridin-7-one.

In the context of the present invention:

The halogen atoms preferentially denote a fluorine, chlorine, bromine or iodine atom.

The alkyl, monohydroxyalkyl, polyhydroxyalkyl, alkylhydroxyalkyl, alkylsulphonyl, carboxyalkyl, aminoalkyl, alkylaminoalkyl and dihydroxyaminoalkyl radicals can be linear or branched.

The alkyl groups in particular denote groups of 1 to 20 carbon atoms such as, for example, methyl, ethyl, propyl, isopropyl, n-propyl, butyl, n-butyl, tert-butyl, pentyl, n-pentyl, isopentyl, n-hexyl, isohexyl, heptyl, octyl, nonyl, decyl, undecyl, dodecyl and pentadecyl groups. The alkyl groups preferably denote a group of 1 to 6 carbon atoms;

these alkyl groups can be substituted; for example, with a halogen atom or a cyano or hydroxyl radical, and can thus represent trifluoromethyl, δ-chloropropyl, β-cyanoethyl or β-hydroxyethyl radicals.

Among the monohydroxyalkyl groups which may be mentioned in particular are hydroxymethyl, hydroxyethyl, hydroxypropyl and hydroxybutyl groups.

Among the polyhydroxyalkyl radicals which may be mentioned in particular are dihydroxyethyl, dihydroxypropyl, trihydroxypropyl and dihydroxybutyl radicals.

The alkoxy groups denote a group —O—R, R representing an alkyl group as defined above.

The alkenyl groups denote a monovalent radical corresponding to the ethylenic carbons, such as, for example, alkyl or 3,3-dimethylallyl.

The acetyloxy groups denote a group —O—CO—R, R representing an alkyl group as defined above.

Among the cycloalkyl radicals which may be mentioned in particular are cyclohexyl and cyclopentyl.

Among the aryl radicals which may be mono- or polycyclic, mention may be made in particular of phenyl and naphthyl groups.

Among the heterocycles, which may be mono- or polycyclic and containing one or more hetero atoms, mention may be made of thiophene, pyrrole, imidazole, pyrazole, triazole, thiazole, furan, benzofuran, benzimidazole, benzothiazole, pyridyl, benzoxazole, quinolyl, quinazolyl, quinoxalyl or naphthyl, rings.

Among the alkylaryl radicals which may be mentioned in particular are benzyl, phenethyl and naphthylmethyl groups.

The aminoaryl groups denote groups NHR, R representing an aryl radical.

In the context of the present invention, the cycloalkyl and aryl radicals and the heterocycles may be substituted or polysubstituted, for example with a halogen, with a $C_1$–$C_4$ alkyl, a $C_1$–$C_4$, alkoxy, a nitro group, a hydroxyl group, a carboxylic group, a $C_1$–$C_4$ acetyloxy group, a carboxamide group, a sulphonamide, sulphonic, nitrile, —$CF_3$ or —$OCF_3$ group or with a cycloalkyl or aryl radical which may be substituted with a $C_1$–$C_4$ alkyl.

In the context of the present invention, the formulae (I) to (XXIII) are not limited to those specifically described, but also comprise the tautomeric forms thereof, when they exist.

For the purposes of the present invention, the cosmetically acceptable salts of the above mentioned compounds can be hydrochlorides, sulphates, hydrobromide or tartrates.

The compositions for dyeing keratin fibres, in particular human keratin fibres such as the hair, in accordance with the present invention are essentially characterized in that they comprise at least one compound containing active methylene as defined above and at least one compound chosen from an aldehyde of formula (XVIII), a ketone of formula (XIX) or (XX), a quinone and a diiminoisoindoline or 3-aminoisoindolone derivative as defined above, in a medium which is suitable for dyeing.

The compound containing active methylene in these compositions is preferably chosen from benzofuran(2H)one, benzoylacetonitrile, 5-amino-2H-pyrazol-3-ol and 4-imino-4,5-dihydrothiazol-2-ylamine.

In one preferred embodiment of the invention, the compound chosen from an aldehyde of formula (XVIII), a ketone of formula (XIX) or (XX), a quinone and a diiminoisoindoline or 3-aminoisoindolone derivative is chosen from naphthoquinone, isatin, N-methylisatin, 3-imino-3H-isoindol-1-ylamine, 4-dimethylaminobenzaldehyde and 4-dimethylaminonaphthaldehyde, The compound containing active methylene may be present in a concentration ranging from 0.01% to 10%, and preferably from 0.05% to 5%, by weight relative to the total weight of the composition.

The compound chosen from an aldehyde of formula (XVIII), a ketone of formula (XIX) or (XX), a quinone and a diiminoisoindoline or 3-aminoisoindolone derivative can be present in a concentration ranging from 0.01% to 10%, and preferably from 0.05% to 5%, by weight relative to the total weight of the composition.

The medium which is suitable for dyeing is preferably an aqueous medium consisting of water and/or of cosmetically acceptable organic solvents, and more particularly alcohols such as ethyl alcohol, isopropyl alcohol, benzyl alcohol and phenethyl alcohol, or glycols or glycol ethers such as, for example, ethylene glycol and its monomethyl, monoethyl and monobutyl ethers, propylene glycol or its ethers such as, for example, propylene glycol monomethyl ether, butylene glycol, dipropylene glycol and diethylene glycol alkyl ethers such as, for example, diethylene glycol monoethyl ether or monobutyl ether, in concentrations of between about 0.5% and 20%, and preferably between about 2% and 10%, by weight relative to the total weight of the composition.

Fatty amides such as mono- and diethanolamides of acids derived from copra, of lauric acid or of oleic acid can also be added to the composition according to the invention, in concentrations of between about 0.05% and 10% by weight.

Surfactants that are well known in the prior art and of anionic, cationic, nonionic, amphoteric or zwitterionic type or mixtures thereof can also be added to the composition according to the invention, preferably in a proportion of between about 0.1% and 50% by weight and advantageously between about 1% and 20% by weight relative to the total weight of the composition.

Thickeners can also be used in a proportion ranging from about 0.2% to 20%.

The said dye composition can also contain various common adjuvants such as antioxidants, fragrances, sequestering agents, dispersants, hair conditioners, preserving agents and opacifiers, as well as any other additive usually used in the dyeing of keratin substances.

Needless to say, a person skilled in the art will take care to select the optional additional compounds mentioned above, such that the advantageous properties intrinsically associated with the dye composition according to the invention are not, or are not substantially, adversely affected by the addition(s) envisaged.

The dye composition according to the invention can be formulated at acidic, neutral or alkaline pH, it being possible for the pH to vary, for example, from 2 to 11 and preferably from 5 to 10, and it being possible for it to be adjusted by means of basifying or acidifying agents or buffers that are previously well known.

Basifying agents which may be mentioned are aqueous ammonia, alkaline carbonates, alkanolamines, for example mono-, di- and triethanolamine and derivatives thereof, sodium hydroxide, potassium hydroxide and the compounds of formula:

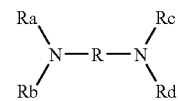

in which R is a propylene residue optionally substituted with a hydroxyl group or a $C_1$–$C_4$, alkyl radical; Ra, Rb, Rc and Rd, simultaneously or independently of each other, represent a hydrogen atom or a $C_1$–$C_4$ alkyl or $C_1$–$C_4$ hydroxyalkyl radical.

The acidifying agents are conventionally mineral or organic acids such as, for example, hydrochloric acid, tartaric acid, citric acid and phosphoric acid.

Among the buffers which may be mentioned, for example, is potassium dihydrogen phosphate/sodium hydroxide.

The composition applied to the hair can be in various forms, such as in the form of a liquid, cream or gel or in any other form which is suitable for dyeing keratin fibres. In particular, it can be packaged under pressure in an aerosol can in the presence of a propellant and can form mousse.

In accordance with the present invention, the process for dyeing keratin fibres, in particular human keratin fibres such as the hair, is essentially characterized in that a component (A) consisting of a composition containing, in a medium which is suitable for dyeing, at least one compound containing active methylene as defined above, and a component (B) consisting of a composition containing, in a medium which is suitable for dyeing, at least one compound chosen from an aldehyde of formula (XVIII), a ketone of formula (XIX) or (XX), a quinone and a diiminoisoindoline or 3-aminoisoindolone derivative such as, for example, one or those defined above, is applied to the said fibres so as to allow the development of a coloration on the said keratin fibres.

In one preferred embodiment of the process of the invention, the components (A) and (B) are mixed together just before use, and the resulting composition is then applied immediately to the keratin fibres, and is left to act on them for 1 to 60 minutes and preferably from 1 to 30 minutes; the keratin fibres are then rinsed, washed with shampoo, rinsed again and then dried.

Another process of the present invention consists essentially in applying component (A) to the keratin fibres, followed or preceded by application of component (B) to the said fibres, in leaving each component to act for 1 to 60 minutes and preferably from 1 to 30 minutes, and in optionally rinsing with water between each application; the keratin fibres are then rinsed, washed with shampoo, rinsed again and then dried.

A subject of the invention is also an agent for dyeing keratin fibres, in particular human hair, characterized in that it consists of components (A) and (B) stored separately, as defined above.

Components (A) and (B) are intended either to be mixed together immediately before use or to be applied successively to the fibres to be treated.

According to one embodiment, the various components (A) and (B) can be packaged in a multi-compartment device also known as a "dyeing kit" comprising all the components intended to be applied for the same dyeing operation on keratin fibres, in particular human keratin fibres such as the hair, in successive applications with or without premixing.

Such devices can comprise a first compartment containing component (A) containing the compound containing active methylene and a second compartment containing component (B) containing the compound chosen from an aldehyde, a ketone, a quinone and a diiminoisoindoline or 3-aminoisoindolone derivative.

Another variant can also consist in storing component (A) or component (B) in an anhydrous solvent medium and in providing a third compartment containing a cosmetically acceptable aqueous medium which is suitable for dyeing. In this case, the contents of the third compartment are mixed, immediately before use, into one or other of the two compartments containing the anhydrous components (A) and (B), or alternatively the three compartments are mixed together before use.

Concrete examples illustrating the invention will now be given.

EXAMPLES

Example 1

The dye composition below was prepared just before use:

| 3-imino-3H-isoindol-1-ylamine | | 0.435 g |
| benzofuran-(2H)-one | | 0.402 g |
| ethyl alcohol | | 30.0 g |
| water | qs | 100 g |

The above composition was applied to locks of natural grey hair containing 90% white hairs, and was left to stand on the hair for 30 minutes. After rinsing with running water and drying, the hair was a lemon yellow shade.

Example 2

The dye composition below was prepared just before use:

| 4-dimethylaminobenzaldehyde | | 0.447 g |
| benzofuran-(2H)-one | | 0.402 g |
| ethyl alcohol | | 30.0 g |
| water | qs | 100 g |

The above composition was applied to locks of permanent-waved grey hair containing 90% white hairs, and was left to stand on the hair for 30 minutes. After rinsing with running water and drying, the hair was a bright orange shade.

Example 3

The dye composition below was prepared just before use:

| 1,4-naphthoquinone | | 0.447 g |
| benzofuran-(2H)-one | | 0.402 g |
| ethyl alcohol | | 30.0 g |
| water | qs | 100 g |

The above composition was applied to locks of permanent-waved grey hair containing 90% white hairs, and was left to stand on the hair for 30 minutes. After rinsing with running water and drying, the hair was a dark violet shade.

Example 4

The dye composition below was prepared just before use:

| isatin | | 0.441 g |
| benzofuran-(2H)-one | | 0.402 g |
| ethyl alcohol | | 30.0 g |
| water | qs | 100 g |

The above composition was applied to locks of bleached hair, and was left to stand on the hair for 30 minutes. After rinsing with running water and drying, the hair was a coppery shade.

Example 5

The dye composition below was prepared just before use:

| 3-imino-3H-isoindol-1-ylamine | | 0.435 g |
| benzoylacetonitrile | | 0.435 g |
| ethyl alcohol | | 30.0 g |
| water | qs | 100 g |

The above composition was applied to locks of bleached hair, and was left to stand on the hair for 30 minutes. After rinsing with running water and drying, the hair was a mustard-yellow shade.

Example 6

The dye composition below was prepared just before use:

| | |
|---|---|
| 4-dimethylaminobenzaldehyde | 0.447 g |
| benzoylacetonitrile | 0.402 g |
| ethyl alcohol | 30.0 g |
| water | qs 100 g |

The above composition was applied to locks of permanent-waved grey hair containing 90% white hairs, and was left to stand on the hair for 30 minutes. After rinsing with running water and drying, the hair was a bright red-orange shade.

Example 7

The dye composition below was prepared just before use:

| | |
|---|---|
| 1,4-naphthoquinone | 0.474 g |
| benzoylacetonitrile | 0.435 g |
| ethyl alcohol | 30.0 g |
| water | qs 100 g |

The above composition was applied to locks of permanent-waved grey hair containing 90% white hairs, and was left to stand on the hair for 30 minutes. After rinsing with running water and drying, the hair was a hazelnut shade.

Example 8

The dye composition below was prepared just before use:

| | |
|---|---|
| isatin | 0.441 g |
| benzoylacetonitrile | 0.435 g |
| ethyl alcohol | 30.0 g |
| water | qs 100 g |

The above composition was applied to locks of bleached hair, and was left to stand on the hair for 30 minutes. After rinsing with running water and drying, the hair was a red-coppery shade.

Example 9

The dye composition below was prepared just before use:

| | |
|---|---|
| 3-imino-3H-isoindol-1-ylamine | 0.435 g |
| 6-hydroxybenzofuran-(2H)-one | 0.450 g |
| ethyl alcohol | 30.0 g |
| water | qs 100 g |

The above composition was applied to locks of permanent-waved grey hair containing 90% white hairs, and was left to stand on the hair for 30 minutes. After rinsing with running water and drying, the hair was a golden yellow shade.

Example 10

The dye composition below was prepared just before use:

| | |
|---|---|
| 4-dimethylaminobenzaldehyde | 0.447 g |
| 6-hydroxybenzofuran-(2H)-one | 0.450 g |
| ethyl alcohol | 30.0 g |
| water | qs 100 g |

The above composition was applied to locks of permanent-waved grey hair containing 90% white hairs, and was left to stand on the hair for 30 minutes. After rinsing with running water and drying, the hair was an orange-yellow shade.

Example 11

The dye composition below was prepared just before use:

| | |
|---|---|
| 1,4-naphthoquinone | 0.474 g |
| 6-hydroxybenzofuran-(2H)-one | 0.450 g |
| ethyl alcohol | 30.0 g |
| water | qs 100 g |

The above composition was applied to locks of permanent-waved grey hair containing 90% white hairs, and was left to stand on the hair for 30 minutes. After rinsing with running water and drying, the hair was a hazelnut shade.

Example 12

The dye composition below was prepared just before use:

| | |
|---|---|
| isatin | 0.441 g |
| 6-hydroxybenzofuran-(2H)-one | 0.450 g |
| ethyl alcohol | 30.0 g |
| water | qs 100 g |

The above composition was applied to locks of permanent-waved grey hair containing 90% white hairs, and was left to stand on the hair for 30 minutes. After rinsing with running water and drying, the hair was a coppery slightly yellow shade.

Example 13

The dye composition below was prepared just before use:

| | |
|---|---|
| 3-imino-3H-isoindol-1-ylamine | 0.435 g |
| 5-amino-2H-pyrazol-3-ol | 0.297 g |
| ethyl alcohol | 30.0 g |
| water | qs 100 g |

The above composition was applied to locks of bleached hair, and was left to stand on the hair for 30 minutes. After rinsing with running water and drying, the hair was a golden-beige shade.

Example 14

The dye composition below was prepared just before use:

| | | |
|---|---|---|
| 4-dimethylaminobenzaldehyde | | 0.447 g |
| 5-amino-2H-pyrazol-3-ol | | 0.297 g |
| ethyl alcohol | | 30.0 g |
| water | qs | 100 g |

The above composition was applied to locks of permanent-waved grey hair containing 90% white hairs, and was left to stand on the hair for 30 minutes. After rinsing with running water and drying, the hair was a orange-yellow shade.

Example 15

The dye composition below was prepared just before use:

| | | |
|---|---|---|
| 1,4-naphthoquinone | | 0.474 g |
| 5-amino-2H-pyrazol-3-ol | | 0.297 g |
| ethyl alcohol | | 30.0 g |
| water | qs | 100 g |

The above composition was applied to locks of permanent-waved grey hair containing 90% white hairs, and was left to stand on the hair for 30 minutes. After rinsing with running water and drying, the hair was a golden brown shade.

Example 16

The dye composition below was prepared just before use:

| | | |
|---|---|---|
| 3-imino-3H-isoindol-1-ylamine | | 0.435 g |
| 3-amino-1-phenyl-2-pyrazolin-5-one | | 0.525 g |
| ethyl alcohol | | 30.0 g |
| water | qs | 100 g |

The above composition was applied to locks of natural grey hair containing 90% white hairs, and was left to stand on the hair for 30 minutes. After rinsing with running water and drying, the hair was a green-yellow shade.

Example 17

The dye composition below was prepared just before use:

| | | |
|---|---|---|
| 4-dimethylaminobenzaldehyde | | 0.447 g |
| 3-amino-1-phenyl-2-pyrazolin-5-one | | 0.525 g |
| ethyl alcohol | | 30.0 g |
| water | qs | 100 g |

The above composition was applied to locks of bleached hair, and was left to stand on the hair for 30 minutes. After rinsing with running water and drying, the hair was a bright orange shade.

Example 18

The dye composition below was prepared just before use:

| | | |
|---|---|---|
| 1,4-naphthoquinone | | 0.474 g |
| 3-amino-1-phenyl-2-pyrazolin-5-one | | 0.525 g |
| ethyl alcohol | | 30.0 g |
| water | qs | 100 g |

The above composition was applied to locks of permanent-waved grey hair containing 90% white hairs, and was left to stand on the hair for 30 minutes. After rinsing with running water and drying, the hair was a dark brown shade.

Example 19

The dye composition below was prepared just before use:

| | | |
|---|---|---|
| 3-imino-3H-isoindol-1-ylamine, HCl | | 0.435 g |
| 4-imino-4,5-dihydrothiazol-2-ylamine | | 0.454 g |
| ethyl alcohol | | 30.0 g |
| water | qs | 100 g |

The above composition was applied to locks of natural grey hair containing 90% white hairs, and was left to stand on the hair for 30 minutes. After rinsing with running water and drying, the hair was a bright orange shade.

Example 20

The dye composition below was prepared just before use:

| | | |
|---|---|---|
| 3-imino-3H-isoindol-1-one | | 0.438 g |
| 4-imino-4,5-dihydrothiazol-2-ylamine HCl | | 0.454 g |
| ethyl alcohol | | 30.0 g |
| water | | qs 100 g |

The above composition was applied to locks of natural grey hair containing 90% white hairs, and was left to stand on the hair for 30 minutes. After rinsing with running water and drying, the hair was a yellow shade.

Example 21

The dye composition below was prepared just before use:

| | | |
|---|---|---|
| 4-dimethylaminobenzaldehyde | | 0.447 g |
| 4-imino-4,5-dihydrothiazol-2-ylamine HCl | | 0.454 g |
| ethyl alcohol | | 30.0 g |
| water | qs | 100 g |
| [lacuna] | | |

The invention claimed is:

1. A process for dyeing at least one keratin fiber, comprising applying to said at least one keratin fiber a composition comprising:

(a) at least one compound comprising at least one active methylene group, wherein said at least one compound comprising at least one active methylene group comprises at least one methylene group substituted with two groups each having an effect chosen from an electron-withdrawing effect and a mesomeric effect, and further wherein said at least one compound comprising at least one active methylene group is chosen from:

1) pyridine derivatives having formula (I):

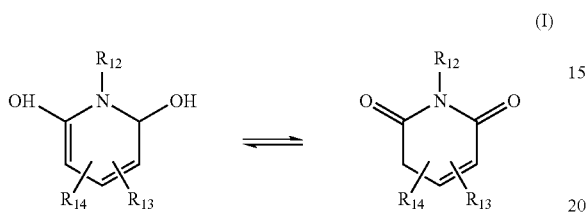

(I)

in which:
R$_{12}$ is chosen from alkyl groups, optionally substituted; and aryl groups, optionally substituted;
R$_{13}$ is chosen from hydrogen; alkyl groups, optionally substituted; and
aryl groups, optionally substituted; and
R$_{14}$ is chosen from hydrogen; nitrile groups; alkyl groups, optionally substituted; and —COOR groups wherein R is chosen from hydrogen and alkyl groups, optionally substituted;

2) derivatives having formula (II):

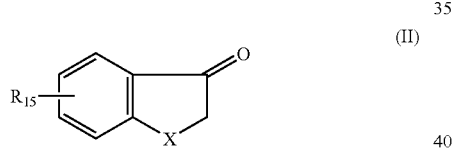

(II)

in which:
X is chosen from oxygen; sulphur; nitrogen; and NR' groups, wherein R' is chosen from alkyl groups; and
R$_{15}$ is chosen from hydrogen; chlorine; bromine; hydroxyl groups; nitro groups; alkyl groups; alkoxy groups; carboxamide groups; sulphonamide groups; and nitrile groups;

and the cosmetically acceptable salts of each of said at least one compounds comprising at least one active methylene group; and (b) at least one compound chosen from aldehydes; ketones; quinones; diiminoisoindoline derivatives; 3-aminoisoindolone derivatives; and the cosmetically acceptable salts of each of said at least one compounds;

wherein when said at least one compound is chosen from aldehydes, said aldehydes are chosen from aldehydes said having formula (III) and the cosmetically acceptable salts thereof:

(III)

in which:
R$_{25}$ is chosen from groups having formula (III A):

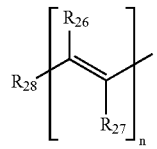

in which:
R$_{26}$ and R$_{27}$, which may be identical or different, are each chosen from hydrogen; alkyl groups; monohydroxyalkyl groups; polyhydroxyalkyl groups; alkylhydroxyalkyl groups; alkoxy groups;
—CF$_3$ groups; and —OCF$_3$ groups;
R$_{26}$ and R$_{27}$, which may be identical or different, may also form, together with the atoms to which they are attached, at least one ring, optionally substituted, chosen from aryl rings; 5-membered heterocyclic rings; and 6-membered heterocyclic rings;
n is an integer ranging from 0 to 3; and
R$_{28}$ is chosen from hydrogen; alkyl groups; monohydroxyalkyl groups; polyhydroxyalkyl groups; alkylhydroxyalkyl groups; alkoxy groups; —CF$_3$ groups; —OCF$_3$ groups; aryl groups, optionally substituted; alkylaryl groups, optionally substituted; 5-membered heterocyclic groups, optionally substituted; and 6-membered hetero cyclic groups, optionally substituted;

wherein when said at least one compound is chosen from ketones, said ketones are chosen from ketones having formula (IV), ketones having formula (V), and the cosmetically acceptable salts thereof:

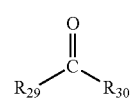

(IV)

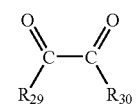

(V)

in which:
—R$_{29}$ is chosen from groups having formula (VI):

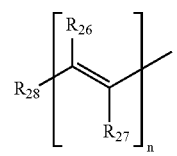

(VI)

in which:
—R$_{26}$ and R$_{27}$, which may be identical or different, are each chosen from hydrogen; alkyl groups; monohydroxyalkyl groups; polyhydroxyalkyl groups; alkylhydroxyalkyl groups; alkoxy groups;

—CF₃ groups; and —OCF₃ groups;

—R₂₆ and R₂₇, which may be identical or different, may also form, together with the atoms to which they are attached, at least one ring, optionally substituted, chosen from aryl rings; 5-membered heterocyclic rings; and 6-membered heterocyclic rings;

—n is an integer ranging from 0 to 3; and

—R₂₈ is chosen from hydrogen; alkyl groups; monohydroxyalkyl groups; polyhydroxyalkyl groups; alkylhydroxyalkyl groups; alkoxy groups; —CF₃ groups; —OCF₃ groups; aryl groups, optionally substituted; alkylaryl groups, optionally substituted; 5-membered heterocyclic groups, optionally substituted; and 6-membered heterocyclic groups, optionally substituted;

—R₃₀ is chosen from alkyl groups; monohydroxyalkyl groups; polyhydroxyalkyl groups; alkylhydroxyalkyl groups; aryl groups, optionally substituted; alkylaryl groups, optionally substituted; 5-membered heterocyclic groups, optionally substituted; and 6-membered heterocyclic groups, optionally substituted; and R₂₉ and R₃₀ may also form, together with the atoms to which they are attached, at least one ring, optionally substituted, chosen from 5-membered aryl rings; 6-membered aryl rings; and heterocyclic rings; it being possible for said at least one ring itself to be attached to at least one additional ring, optionally substituted, chosen from 5-membered aryl rings; 6-membered aryl rings; and heterocyclic rings;

and with the proviso that a coloration of said at least one keratin fiber is achieved without an oxidizing agent.

2. A process according to claim 1, wherein said at least one keratin fiber is a human keratin fiber.

3. A process according to claim 2, wherein said human keratin fiber is hair.

4. A process according to claim 1, wherein at least one of said heterocyclic rings comprises at least one heteroatom chosen from sulphur and nitrogen.

5. A process according to claim 1, wherein said at least one compound comprising at least one active methylene group is chosen from 2,6-dihydroxy-3-cyano-4-methylpyridine; cyanopyridones; aminonitropyridones; and aminocyanopyridones.

6. A process according to claim 1, wherein said at least one compound comprising at least one active methylene group is chosen from N-methyl-3-cyano-4-methyl-6-hydroxy-2-pyridone; N-ethyl-3-cyano-4-methyl-6-hydroxy-2-pyridone; N-b-methoxyethyl-3-cyano-4-methyl-6-hydroxy-2-pyridone; 2,6-dihydroxy-3-cyano-4-methylpyridine; N-b-hydroxyethyl-3-cyano-4-methyl-6-hydroxy-2-pyridone; N-butyl-3-cyano-4-methyl-6-hydroxy-2-pyridone; and N-phenyl-3-cyano-4-methyl-6-hydroxy-2-pyridone.

7. A process according to claim 1, wherein said at least one compound comprising at least one active methylene group is chosen from 6-hydroxybenzofuran-(2H)-one and benzofuran-(2H)-one.

8. A process according to claim 1, wherein said at least one compound comprising at least one active methylene group is chosen from:
   1,3-dihydroindol-2-one;
   3H-benzofuran-2-one;
   1-methyl-1,3-dihydroindol-2-one;
   5-methoxy-3H-benzofuran-2-one;
   5-nitro-1,3-dihydroindol-2-one;
   1-methyl-5-nitro-1,3-dihydroindol-2-one;
   6-methoxy-1,3-dihydroindol-2-one;
   5-chloro-1,3-dihydroindol-2-one;
   5,6-difluoro-1,3-dihydroindol-2-one;
   6-hydroxy-5-methoxy-1,3-dihydroindol-2-one;
   5,6-dimethoxy-1,3-dihydroindol-2-one; and
   6-trifluoromethyl-1,3-dihydroindol-2-one.

9. A process according to claim 1, wherein said at least one compound is chosen from benzaldehyde; 2-monohydroxybenzaldehyde;
3-monohydroxybenzaldehyde; 4-monohydroxybenzaldehyde;
2-monomethoxybenzaldehyde; 3-monomethoxybenzaldehyde;
4-monomethoxybenzaldehyde; 2-monomethylbenzaldehyde;
3-monomethylbenzaldehyde; 4-monomethylbenzaldehyde; (2,3)-dihydroxybenzaldehyde; (2,4)-dihydroxybenzaldehyde; (2,5)-dihydroxybenzaldehyde;
(2,6)-dihydroxybenzaldehyde; (3,5)-dihydroxybenzaldehyde;
(2,3)-dimethoxybenzaldehyde; (2,4)-dimethoxybenzaldehyde;
(2,5)-dimethoxybenzaldehyde; (2,6)-dimethoxybenzaldehyde;
(3,5)-dimethoxybenzaldehyde; vanillin; isovanillin; syringaldehyde; orthophthalalclehyde; isophthalaldehyde; terephthalaldehyde; (2,3)-dimethylbenzaldehyde;
(2,4)-dimethylbenzaldehyde; (2,5)-dimethylbenzaldehyde; (2,6)-dimethylbenzaldehyde;
(3,5)-dimethylbenzaldehyde; 4-isopropylbenzaldehyde; 4-dimethylaminobenzaldehyde;
4-diethylaminobenzaldehyde; piperonal; (2,6)-dimethyl-4-hydroxybenzaldehyde;
(3,5)-dimethyl-4-hydroxybenzaldehyde; 2-mononitrobenzaldehyde;
3-mononitrobenzaldehyde; 4-mononitrobenzaldehyde; 2-hydroxy-3-methoxy-benzaldehyde; 2-hydroxy-4-methoxybenzaldehyde; 2-hydroxy-5-methoxy-benzaldehyde; 2-hydroxy-6-methoxybenzaldehyde; 4-methyithiobenzaldehyde;
(2,3,4)-trihydroxybenzaldehyde; (2,4,6)-trihydroxybenzaldehyde;
(3,4,5)-trihydroxybenzaldehyde; (2,4,5)-trihydroxybenzaldehyde; methyl 2-formyl-benzoate; methyl 3-formylbenzoate; methyl 4-formylbenzoate;
2-mono(2-hydroxyethoxy)belzaldehyde; 3-mono(2-hydroxyethoxy)benzaldehyde;
4-mono(2-hydroxyethoxy)benzaldehyde, 4-nitro-3-hydroxybenzaldehyde; 3-nitro-4-hydroxybenzaldehyde; 2-nitro-4-hydroxybenzaldehyde; 3-nitro-2-hydroxybenzaldehyde;
2-monotrifluorobenzaldehyde; 3-monotrifluorobenzaldehyde;
4-monotrifluorobenzaldehyde; 2,3-dihydroxy-4-methoxybeflzaldehyde; 3,4-dihydroxy-5-methoxy benzaldehyde; 3,5-dihydroxy-4-methoxybenzaldehyde; 3-methoxy-2-nitrobenzaldehyde; 4-methoxy-2-nitrobenzaldehyde; 2-methoxy-3-nitrobenzaldehyde;
4-methoxy-3-nitro-benzaldehyde; (2,3,4)-trimethoxybenzaldehyde;
(2,4,6)-trimethoxybenzaldehyde; (3,4,5)-trimethoxybenzaldehyde;
(2,4,5)-trimethoxybenzaldehyde; 5-nitrovanillin; (2,4)-dinitrobenzaldehyde;
(2,6)-dinitrobenzaldehyde; pentamethylbenzaldehyde; 4-methylsulphonylbenzaldehyde;

2-monoformylphenoxyacetic acid; 3-monoformylphenoxyacetic acid;
4-monoformylphenoxyacetic acid; 4-diethylaminosalicylaldehyde; 4-(3-dimethylaminopropoxy)benzaldehyde; 2,3-dihydrobenzo(b)furan-5-carboxaldehyde;
1-naphthaldehyde; 2-naphthaldehyde; 6-carboxaldehyde-1,4-benzodioxane;
5-carboxaldehyde-1,4-benzodioxane; 2-monohydroxy-1-naphthaldehyde;
4-monohydroxy-1-naphthaldehyde; 1-monohydroxy-2-naphthaldehyde; 1-(4-formylphenyl)imidazole; 4-pyrrolidinobenzaldehyde; 2-monomethoxy-1-naphthaldehyde;
4-monomethoxy-1-naphthaldehyde; 2,3-dimethylchroman-6-carboxaldehyde; 2,3,6,7-tetrahydro-1H,5H-pyrido-(3,2,1-IJ)quinoline-9-carbaldehyde; 4-dimethylamino-1-naphthaldehyde; 9-anthraldehyde; 3-nitro-4-pyrrolidinobenzaldehyde; 3-nitro-4-piperidino benzaldehyde; 3-nitro-4-morpholinobenzaldehyde; pyridine-2-monocarboxaldehyde; pyridine-3-monocarboxaldehyde; pyridine-4-monocarboxaldehyde; 2,6-pyridino-dicarboxaldehyde; 5-formyl-6-methyluracil;
pyridoxal; quinoline-2-monocarboxaldehyde; quinoline-3-monocarboxaldehyde;
quinoline-4-monocarboxaldehyde; 8-hydroxyquinoline-2-carboxaldehyde; 2-furaldehyde;
3-furaldehyde; 2-thienylcarboxaldehyde; 3-thienylcarboxaldehyde;
2-imidazocarboxaldehyde; 3-imidazocarboxaldehyde; 2-pyrrolecarboxaldehyde; 5-nitro-2-furaldehyde; 5-(dimethylamino)-2-furaldehyde; 2,5-thiophenedicarboxaldehyde;
2,3-thiophenedicarboxaldehyde; pyrazole-3-carbaldehyde; 5-nitro-2-thiophenecarboxaldehyde; 5-nitro-3-thiophenecarboxaldehyde; indole-3-carboxaldehyde; N-methylindole-3-carboxaldehyde; 2-methylindole-3-carboxaldehyde;
4-monomethylindolecarboxaldehyde; 5-monomethylindolecarboxaldehyde;
6-monomethylindolecarboxaldehyde; 7-monomethylindolecarboxaldehyde; and
5-formyl-2-furansulphonic acid.

10. A process according to claim 1, wherein said at least one compound is chosen from 2,3-indolinedione; 2,3-butanedione; 2,3-pentanedione; (2,3)-hexanedione; (3,4)-hexanedione; 1-phenyl-1,2-propanedione; benzil; furil; 2,2'-pyridil; nitrobenzil; anisil; 3,3'-dimethoxybenzil; 4,4'-bis(dimethyl-amino)benzil; camphoroquinone; cyclohexane-1,2-dione; isatin; N-methylisatin; 4-monomethylisatin; 5-monomethylisatin; 6-monomethylisatin; 7-monomethylisatin; (4,5)-dimethylisatin; (4,7)-dimethylisatin; (5,7)-dimethylisatin; (6,7)-dimethylisatin; N-ethylisatin; N-hydroxymethylisatin; 5-monomethoxyisatin; 6-monomethoxyisatin; 7-monomethoxyisatin; 4-monochloroisatin; 5-monochloroisatin; 6-monochloroisatin; 7-monochloroisatin; 4-monobromoisatin; 5-monobromoisatin; 6-monobromoisatin; 7-monobromoisatin; N-isopropylisatin; N-butylisatin; N-propylisatin; 5-nitroisatin; isatin-5-sulphonic acid; 2,4,5-trihydroxypyrimidine; alloxan; 1,3-dimethylhexahydro-2,4,5,6-pyrimidinetetraone; ninhydrin; chinisatin; 1,3-indenedione; squaric acid; croconic acid; 3,4-dimethoxy-3-cyclobutene-1,2-dione; 3-ethoxy-3-cyclobutene-1,2-dione; 4-ethoxy-3-cyclobutene-1,2-dione; 3-isopropoxy-3-cyclobutene-1,2-dione; 4-isopropoxy-3-cyclobutene-1,2-dione; 3,4-di-N-butoxy-3-cyclobutene-1,2-dione; rhodizonic acid; oxindole; N-methyl-2-indolinone; N-methylnitro-2-indolinone; 6-methoxyoxindole; 5,6-dimethoxyoxindole; 5-monochlorooxindole; and 6-monochlorooxindole.

11. A process according to claim 1, wherein said salts are chosen from hydrochlorides; sulphates; hydrobromides; and tartrates.

12. A process according to claim 1, wherein said at least one compound is chosen from naphthoquinone; isatin; N-methylisatin; 3imino-3H-isoindol-1-ylamine; 4-dimethylaminobanzaldehyde; and 4-dimethylaminonaphthaldehyde.

13. A process according to claim 1, wherein said at least one compound comprising at least one active methylene group is present in said composition in a concentration ranging from 0.01% to 10% by weight relative to the total weight of said composition.

14. A process according to claim 13, wherein said at least one compound comprising at least one active methylene group is present in said composition in a concentration ranging from 0.05% to 5% by weight relative to the total weight of said composition.

15. A process according to claim 1, wherein said at least one compound is present in said composition in a concentration ranging from 0.01% to 10% by weight relative to the total weight of said composition.

16. A process according to claim 15, wherein said at least one compound is present in said composition in a concentration ranging from 0.05% to 5% by weight relative to the total weight of said composition.

17. A composition for dyeing at least one keratin fiber comprising:
(a) at least one compound comprising at least one active methylene group, wherein said at least one compound comprising at least one active methylene group comprises at least one methylene group substituted with two groups each having an effect chosen from an electron-withdrawing effect and a mesomeric effect, and further wherein said at least one compound comprising at least one active methylene group is chosen from:
1) pyridine derivatives having formula (I):

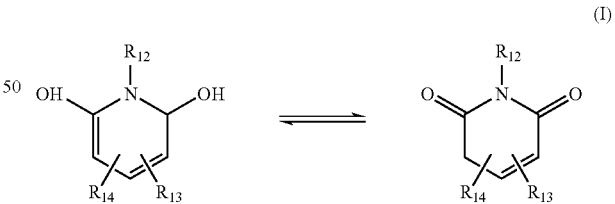

in which:
$R_{12}$ is chosen from alkyl groups, optionally substituted; and aryl groups, optionally substituted;
$R_{13}$ is chosen from hydrogen; alkyl groups, optionally substituted; and
aryl groups, optionally substituted; and
$R_{14}$ is chosen from hydrogen; nitrile groups; alkyl groups, optionally substituted; and —COOR groups wherein R is chosen from hydrogen and alkyl groups, optionally substituted;

2) derivatives having formula (II):

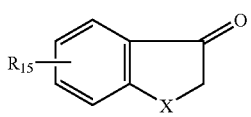

(II)

in which:
X is chosen from oxygen; sulphur; nitrogen; and NR' groups, wherein R' is chosen from alkyl groups; and
$R_{15}$ is chosen from hydrogen; chlorine; bromine; hydroxyl groups; nitro groups; alkyl groups; alkoxy groups; carboxamide groups; sulphonamide groups; and nitrile groups;
and the cosmetically acceptable salts of each of said at least one compounds comprising at least one active methylene group; and (b) at least one compound chosen from dehydes; ketones; diiminoisoindoline derivatives; 3-aminoisoindolone derivatives; and the cosmetically acceptable salts of each of said at least one compound;
wherein when said at least one compound is chosen from aldehydes, said aldehydes are chosen from aldehydes said having formula (III) and the cosmetically acceptable salts thereof:

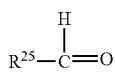

(III)

in which:
—$R_{25}$ is chosen from groups having formula (III A)

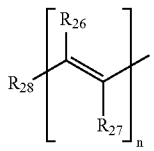

in which:
—$R_{26}$ and $R_{27}$, which may be identical or different, are each chosen from hydrogen; alkyl groups; monohydroxyalkyl groups; polyhydroxyalkyl groups; alkylhydroxyalkyl groups; alkoxy groups; —$CF_3$ groups; and —$OCF_3$ groups;
—$R_{26}$ and $R_{27}$, which may be identical or different, may also form, together with the atoms to which they are attached, at least one ring, optionally substituted, chosen from aryl rings; 5-membered heterocyclic rings; and 6-membered heterocyclic rings;
—n is an integer ranging from 0 to 3; and
—$R_{28}$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered hetero cyclic groups, optionally substituted;
wherein when said at least one compound is chosen from ketones, said ketones are chosen from ketones having formula (IV), ketones having formula (V), and the and the cosmetically acceptable salts thereof:

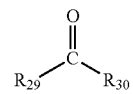

(IV)

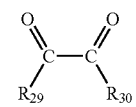

(V)

in which:
$R_{29}$ is chosen from groups having formula (VI):

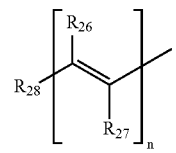

(VI)

in which:
$R_{26}$ and $R_{27}$, which may be identical or different, are each chosen from hydrogen; alkyl groups; monohydroxyalkyl groups; polyhydroxyalkyl groups; alkylhydroxyalkyl groups; alkoxy groups; —$CF_3$ groups; and —$OCF_3$ groups;
$R_{26}$ and $R_{27}$, which may be identical or different, may also form, together with the atoms to which they are attached, at least one ring, optionally substituted, chosen from aryl rings; 5-membered heterocyclic rings; and 6-membered heterocyclic rings;
n is an integer ranging from 0 to 3; and
$R_{28}$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered heterocyclic groups, optionally substituted;
$R_{30}$ is chosen from alkyl groups; monohydroxyalkyl groups; polyhydroxyalkyl groups; alkylhydroxyalkyl groups; aryl groups, optionally substituted; alkylaryl groups, optionally substituted; 5-membered heterocyclic groups, optionally substituted; and 6-membered heterocyclic groups, optionally substituted; and
$R_{29}$ and $R_{30}$ may also form, together with the atoms to which they are attached, at least one ring, optionally substituted, chosen from 5-membered aryl rings; 6-membered aryl rings; and heterocyclic rings; it being possible for said at least one ring itself to be attached to at least one additional ring, optionally substituted, chosen from 5-membered aryl rings; 6-membered aryl rings; and heterocyclic rings;
and with the proviso that said composition does not comprise an oxidizing agent.

18. A composition according to claim 17, wherein said at least one keratin fiber is a human keratin fiber.

19. A composition according to claim 18, wherein said human keratin fiber is hair.

20. A composition according to claim 17, wherein at least one of said heterocyclic rings comprises at least one heteroatom chosen from sulphur and nitrogen.

21. A composition according to claim 17, further comprising at least one medium suitable for dyeing.

22. A composition according to claim 17, said composition having a pH ranging from 2 to 11.

23. A composition according to claim 22, wherein said pH ranges from 5 to 10.

24. A composition according to claim 17, wherein said at least one compound comprising at least one active methylene group is chosen from 2,6-dihydroxy-3-cyano-4-methylpyridine; cyanopyridones; aminonitropyridones; and aminocyanopyridones.

25. A composition according to claim 17, wherein said at least one compound comprising at least one active methylene group is chosen from N-methyl-3-cyano-4-methyl-6-hydroxy-2-pyridone; N-ethyl-3-cyano-4-methyl-6-hydroxy-2-pyridone; N-b-methoxyethyl-3-cyano-4-methyl-6-hydroxy-2-pyridone; 2,6-dihydroxy-3-cyano-4-methylpyridine; N-b-hydroxyethyl-3-cyano-4-methyl-6-hydroxy-2-pyridone; N-butyl-3-cyano-4-methyl-6-hydroxy-2-pyridone; and N-phenyl-3-cyano-4-methyl-6-hydroxy-2-pyridone.

26. A composition according to claim 17, wherein said at least one compound comprising at least one active methylene group is chosen from 6-hydroxybenzofuran-(2H)-one and benzofuran-(2H)-one.

27. A composition according to claim 17, wherein said at least one compound comprising at least one active methylene group is chosen from:
1,3-dihydroindol-2-one;
3H-benzofuran-2-one;
1-methyl-1,3-dihydroindol-2-one;
5-methoxy-3H-benzofuran-2-one;
5-nitro-1,3-dihydroindol-2-one;
1-methyl-5-nitro-1,3-dihydroindol-2-one;
6-methoxy-1,3-dihydroindol-2-one;
5-chloro-1,3-dihydroindol-2-one;
5,6-difluoro-1,3-dihydroindol-2-one;
6-hydroxy-5-methoxy-1,3-dihydroindol-2-one;
5,6-dimethoxy-1,3-dihydroindol-2-one; and
6-trifluoromethyl-1,3-dihydroindol-2-one.

28. A composition according to claim 17, wherein said at least one compound comprising at least one active methylene group is chosen from 2-phenyl-3,5-dihydroimidazol-4-one and 3-methyl-2-p-tolyl-3,5-dihydroimidazol-4-one.

29. A composition according to claim 17, wherein said at least one compound is chosen from benzaldehyde; 2-monohydroxybenzaldehyde; 3-monohydroxybenzaldehyde; 4-monohydroxybenzaldehyde; 2-monomethoxy-benzaldehyde; 3-monomethoxybenzaldehyde; 4-monomethoxybenzaldehyde; 2-monomethylbenzaldehyde; 3-monomethylbenzaldehyde; 4-monomethylbenzaldehyde; (2,3)-dihydroxybenzaldehyde; (2,4)-dihydroxybenzaldehyde; (2,5)-dihydroxybenzaldehyde; (2,6)-dihydroxybenzaldehyde; (3,5)-dihydroxybenzaldehyde; (2,3)-dimethoxybenzaldehyde; (2,4)-dimethoxybenzaldehyde; (2,5)-dimethoxybenzaldehyde; (2,6)-dimethoxybenzaldehyde (3,5)-dimethylbenzaldehyde; vanillin; isovanillin; syringaldehyde; orthophthalaldehyde; isophthalaldehyde; terephthalaldehyde; (2,3)-dimethylbenzaldehyde (2,4)- dimethylbenzaldehyde; (2,5)-dimethylbenzaldehyde; (2,6)-dimethylbenzaldehyde; (3,5)-dimethylbenzaldehyde; 4-isopropylbenzaldehyde; 4-dimethylaminobenzaldehyde; 4-diethylaminobenzaldehyde; piperonal; (2,6)-dimethyl-4-hydroxybenzaldehyde; (3,5)-dimethyl-4-hydroxybenzaldehyde; 2-mononitrobenzaldehyde; 3-mononitrobenzaldehyde; 4-mononitrobenzaldehyde; 2-hydroxy-3-methoxybenzaldehyde; 2-hydroxy-4-methoxybenzaldehyde; 2-hydroxy-5-methoxybenzaldehyde; 2-hydroxy-6-methoxybenzaldehyde; 4-methylthiobenzaldehyde; (2,3,4)-trihydroxybenzaldehyde; (2,4,6)-trihydroxybenzaldehyde; (3,4,5)-trihydroxybenzaldehyde; (2,4,5)-trihydroxybenzaldehyde; methyl 2-formylbenzoate; methyl 3-formylbenzoate; methyl 4-formylbenzoate; 2-mono(2-hydroxyethoxy)benzaldehyde 3-mono(2-hydroxyethoxy)benzaldehyde; 4-mono(2-hydroxyethoxy)benzaldehyde; 4-nitro-3-hydroxybenzaldehyde; 3-nitro-4-hydroxybenzaldehyde; 2-nitro-4-hydroxybenzaldehyde; 3-nitro-2-hydroxybenzaldehyde; 2-monotrifluorobenzaldehyde; 3-monotrifluorobenzaldehyde; 4-monotrifluorobenzaldehyde; 2,3-dihydroxy-4-methoxybenzaldehyde; 3,4-dihydroxy-5-methoxy benzaldehyde; 3,5-dihydroxy-4-methoxybenzaldehyde; 3-methoxy-2-nitrobenzaldehyde; 4-methoxy-2-nitrobenzaldehyde; 2-methoxy-3-nitrobenzaldehyde; 4-methoxy-3-nitro-benzaldehyde; (2,3,4)-trimethoxybenzaldehyde; (2,4,6)-trimethoxybenzaldehyde (3,4,5)-trimethoxybenzaldehyde (2,4,5)-trimethoxybenzaldehyde; 5-nitrovanillin; (2,4)-dinitrobenzaldehyde (2,6)-dinitrobenzaldehyde pentamethylbenzaldehyde 4-methylsulphonylbenzaldehyde; 2-monoformylphenoxyacetic acid; 3-monoformylphenoxyacetic acid; 4-monoformylphenoxyacetic acid; 4-diethylaminosalicylaldehyde 4-(3-dimethylaminopropoxy)benzaldehyde; 2,3-dihydrobenzo(b)furan-5-carboxaldehyde; 1-naphthaldehyde; 2-naphthaldehyde 6-carboxaldehyde-1,4-benzodioxane; 5-carboxaldehyde-1,4-benzodioxane 2-monohydroxy-1-naphthaldehyde; 4-monohydroxy-1-naphthaldehyde; 1-monohydroxy-2-naphthaldehyde; 1(4-formyl-phenyl)imidazole; 4-pyrrolidinobenzaldehyde; 2-monomethoxy-1-naphthaldehyde; 4-monomethoxy-1-naphthaldehyde; 2,3-dimethylchroman-6-carboxaldehyde; 2,3,6,7-tetrahydro-1H,5H-pyrido-(3,2,1-IJ)quinoline-9-carbaldehyde; 4-dimethyl-amino-1-naphthaldehyde; 9-anthraldehyde; 3-nitro-4-pyrrolidinobenzaldehyde; 3-nitro-4-piperidinobenzaldehyde; 3-nitro-4-morpholinobenzaldehyde; pyridine-2-monocarboxaldehyde; pyridine-3-monocarboxaldehyde; pyridine-4-monocarboxaldehyde; 2,6-pyridinodicarboxaldehyde; 5-formyl-6-methyluracil; pyridoxal; quinoline-2-monocarboxaldehyde; quinoline-3-monocarboxaldehyde; quinoline-4-monocarboxaldehyde; 8-hydroxyquinoline-2-carboxaldehyde; 2-furaldehyde; 3-furaldehyde; 2-thienylcarboxaldehyde; 3-thienylcarboxaldehyde; 2-imidazocarboxaldehyde; 3-imidazocarboxaldehyde; 2-pyrrolecarboxaldehyde; 5-nitro-2-furaldehyde; 5-(dimethylamino)-2-furaldehyde; 2,5-thiophenedicarboxaldehyde; 2,3-thiophenedicarboxaldehyde; pyrazole-3-carbaldehyde; 5-nitro-2-thiophenecarboxaldehyde; 5-nitro-3-thiophenecarboxaldehyde; indole-3-carboxaldehyde; N-methylindole-3-carboxaldehyde; 2-methylindole-3-carboxaldehyde; 4monomethylindolecarboxaldehyde; 5-monomethylindolecarboxaldehyde; 6-monomethylindolecarboxaldehyde; 7-monomethylindolecarboxaldehyde; and 5-formyl-2-furansulphonic acid.

30. A composition according to claim 17, wherein said at least one compound is chosen from 2,3-indolinedione; 2,3-butanedione; 2,3-pentanedione (2,3)-hexanedione; (3,4)-hexanedione; 1-phenyl-1,2-propanedione; benzil; furil; 2,2'-pyridil; nitrobenzil; anisil; 3,3'-dimethoxybenzil; 4,4'-bis(dimethylamino)benzil; camphoroquinone; cyclohexane-1,2-dione; isatin; N-methylisatin; 4-monomethylisatin;

5-monomethylisatin; 6-monomethylisatin; 7-monomethylisatin; (4, 5)-dimethylisatin; (4,7)-dimethylisatin; (5,7)-dimethylisatin; (6,7)-dimethylisatin; N-ethylisatin; N-hydroxymethylisatin; 5-monomethoxyisatin; 6-monomethoxyisatin; 7-monomethoxyisatin; 4-monochloroisatin; 5-monochloroisatin; 6-monochloroisatin; 7-monochloroisatin; 4-monobromoisatin; 5-monobromoisatin; 6-monobromoisatin; 7-monobromoisatin; N-isopropylisatin; N-butylisatin; N-propylisatin; 5-nitroisatin; isatin-5-sulphonic acid; 2,4,5-trihydroxypyrimidine; alloxan; 1,3-dimethylhexahydro-2,4,5,6-pyrimidinetetraone; ninhydrin; chinisatin; 1,3-indenedione; squaric acid; croconic acid; 3,4-dimethoxy-3-cyclobutene-1,2-dione; 3-ethoxy-3-cyclobutene-1,2-dione; 4-ethoxy-3-cyclobutene-1,2-dione; 3-isopropoxy-3-cyclobutene-1,2-dione; 4-isopropoxy-3-cyclobutene-1,2-dione; 3,4-di-N-butoxy-3-cyclobutene-1,2-dione; rhodizonic acid; oxindole; N-methyl-2-indolinone; N-methylnitro-2-indolinone; 6-methoxyoxindole; 5,6-dimethoxyoxindole; 5-monochlorooxindole; and 6-monochlorooxindole.

31. A composition according to claim 17, wherein said salts are chosen from hydrochlorides; sulphates; hydrobromides; and tartrates.

32. A composition according to claim 17, wherein said at least one compound is chosen from naphthoquinone; isatin; N-methylisatin; 3-imino-3H-isoindol-1-ylamine; 4-dimethylaminobenzaldehyde; and 4-dimethylaminonaphthaldehyde.

33. A composition according to claim 17, wherein said at least one compound comprising at least one active methylene group is present in said composition in a concentration ranging from 0.01% to 10% by weight relative to the total weight of said composition.

34. A composition according to claim 33, wherein said at least one compound comprising at least one active methylene group is present in said composition in a concentration ranging from 0.05% to 5% by weight relative to the total weight of said composition.

35. A composition according to claim 17, wherein said at least one compound is present in said composition in a concentration ranging from 0.01% to 10% by weight relative to the total weight of said composition.

36. A composition according to claim 35, wherein said at least one compound is present in said composition in a concentration ranging from 0.05% to 5% by weight relative to the total weight of said composition.

37. A composition according to claim 17, further comprising at least one fatty amide.

38. A composition according to claim 37, wherein said at least one fatty amide is chosen from monoethanolamides of acids derived from copra; monoethanolamides of lauric acid; monoethanolamides of oleic acid; diethanolamides of acids derived from copra; diethanolamides of lauric acid; and diethanolamides of oleic acid.

39. A composition according to claim 37, wherein said at least one fatty amide is present in a concentration ranging from 0.05% to 10% by weight relative to the total weight of said composition.

40. A composition according to claim 17, further comprising at least one surfactant.

41. A composition according to claim 40, wherein said at least one surfactant is chosen from anionic surfactants; cationic surfactants; nonionic surfactants; amphoteric surfactants; and zwitterionic surfactants.

42. A composition according to claim 40, wherein said at least one surfactant is present in a concentration ranging from about 0.1% to about 50% by weight relative to the total weight of said composition.

43. A composition according to claim 42, wherein said at least one surfactant is present in a concentration ranging from about 1% to about 20% by weight relative to the total weight of said composition.

44. A composition according to claim 17, further comprising at least one thickener.

45. A composition according to claim 44, wherein said at least one thickener is present in a concentration ranging from about 0.2% to about 20% by weight relative to the total weight of said composition.

46. A composition according to claim 17, further comprising at least one cosmetically acceptable adjuvant chosen from antioxidants; fragrances; sequestering agents; dispersants; hair conditioners; preserving agents; and opacifiers.

47. A composition according to claim 17, wherein said composition is in the form of a liquid, a cream or a gel.

48. A composition according to claim 21, wherein said at least one medium suitable for dyeing is an aqueous medium chosen from water and organic solvents.

49. A composition according to claim 48, wherein said organic solvents are chosen from alcohols; glycols; glycol ethers; and mixtures thereof.

50. A composition according to claim 21, wherein said at least one medium suitable for dyeing is present in a concentration ranging from 0.5% to 20% by weight relative to the total weight of said composition.

51. A multi-compartment device or dyeing kit, wherein said device or dyeing kit comprises at least two compartments, wherein:

(a) a first compartment comprises a component (A); and (b) a second compartment comprises a component (B);

wherein said component (A) comprises a composition which comprises at least one compound comprising at least one active methylene group which comprises at least one methylene group substituted with two groups each having an effect chosen from an electron-withdrawing effect and a mesomeric effect, wherein said at least one compound comprising at least one active methylene group is chosen from:

1) pyridine derivatives having formula (I):

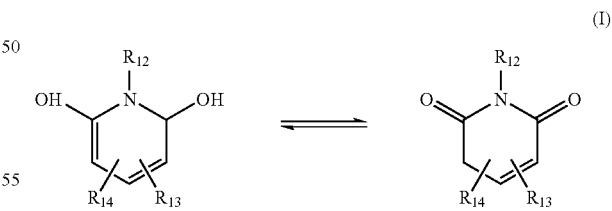

in which:

$R_{12}$ is chosen from alkyl groups, optionally substituted; and aryl groups, optionally substituted;

$R_{13}$ is chosen from hydrogen; alkyl groups, optionally substituted; and aryl groups, optionally substituted; and $R_{14}$ is chosen from hydrogen; nitrile groups; alkyl groups, optionally substituted; and —COOR groups wherein R is chosen from hydrogen and alkyl groups, optionally substituted;

2) derivatives having formula (II):

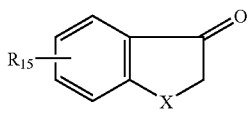

in which:
X is chosen from oxygen; sulphur; nitrogen; and NR' groups, wherein R' is chosen from alkyl groups; and
$R_{15}$ is chosen from hydrogen; chlorine; bromine; hydroxyl groups; nitro groups; alkyl groups; alkoxy groups; carboxamide groups; sulphonamide groups; and nitrile groups;
and the cosmetically acceptable salts of each of said at least one compounds comprising at least one active methylene group; and
wherein said component (B) comprises at least one component (B) comprising a composition which comprises a composition which comprises at least one compound chosen from aldehydes; ketones; quinones; diiminoisoindoline derivatives; 3-amimoisoindolone derivatives; and the cosmetically acceptable salts of each of said at least one compounds;
wherein when said at least one compound is chosen from aldehydes, said aldehydes are chosen from aldehydes said having formula (III) and the cosmetically acceptable salts thereof:

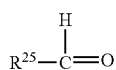

in which:
—$R_{25}$ is chosen from groups having formula (III A):

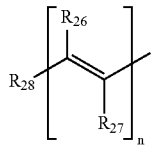

in which:
—$R_{26}$ and $R_{27}$, which may be identical or different, are each from hydrogen; Alkyl groups; monohydroxyalkyl groups; polyhydroxyalkyl groups; alkylhydroxyalkyl groups; alkoxy groups;
$CF_3$ groups; and —$OCF_3$ groups;
—$R_{26}$ and $R_{27}$, which may be identical or different, may also form, together with the atoms to which they are attached, at least one ring, optionally substituted, chosen from aryl rings; 5-membered heterocyclic rings; and 6-membered heterocyclic rings;
—n is an integer ranging from 0 to 3; and
—$R_{28}$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered heterocyclic groups, optionally substituted;
wherein when said at least one compound is chosen from ketones, said ketones are chosen from ketones having formula (IV), ketones having formula (V), and the cosmetically acceptable salts thereof:

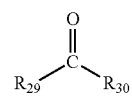

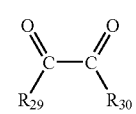

in which:
$R_{29}$ is chosen from groups having formula (VI):

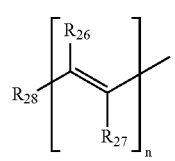

in which:
$R_{26}$ and $R_{27}$, which may be identical or different, are each chosen from hydrogen; alkyl groups; monohydroxyalkyl groups; polyhydroxyalkyl groups; alkylhydroxyalkyl groups; alkoxy groups;
—$CF_3$ groups; and —$OCF_3$ groups;
$R_{26}$ and $R_{27}$, which may be identical or different, may also form, together with the atoms to which they are attached, at least one ring, optionally substituted, chosen from aryl rings; 5-membered heterocyclic rings; and 6-membered heterocyclic rings;
n is an integer ranging from 0 to 3; and
$R_{28}$ is chosen from hydrogen; alkyl groups; monohydroxyalkyl groups; polyhydroxyalkyl groups; alkylhydroxyalkyl groups; alkoxy groups; —$CF_3$ groups; —$OCF_3$ groups; aryl groups, optionally substituted; alkylaryl groups, optionally substituted; 5-membered heterocyclic groups, optionally substituted; and 6-membered heterocyclic groups, optionally substituted;
$R_{30}$ is chosen from alkyl groups; monohydroxyalkyl groups; polyhydroxyalkyl groups; alkylhydroxyalkyl groups; aryl groups, optionally substituted; alkylaryl groups, optionally substituted; 5-membered heterocyclic groups, optionally substituted; and 6-membered heterocyclic groups, optionally substituted; and —$R_{29}$ and $R_{30}$ may also form, together with the atoms to which they are attached, at least one ring, optionally substituted, chosen from 5-membered aryl rings; 6-membered aryl rings; and heterocyclic rings; it being possible for said at least one ring itself to be attached to at least one additional ring, optionally substituted, chosen from 5-membered aryl rings; 6-membered aryl rings; and heterocyclic rings; with the proviso that said device or dyeing kit does not comprise an oxidizing agent.

52. A multi-compartment device or dyeing kit according to claim 51, wherein said salts are chosen from hydrochlorides; sulphates; hydrobromides; and tartrates.

53. A multi-compartment device or dyeing kit according to claim 51, wherein at least one component chosen from said component (A) and said component (B) is in the form of an anhydrous composition; and wherein said device or dyeing kit comprises a third compartment comprising a cosmetically acceptable aqueous medium which is suitable for dyeing and which is intended to be mixed, before use, into at least one compartment chosen from said first compartment comprising a component (A) and said second compartment comprising a component (B).

* * * * *

UNITED STATES PATENT AND TRADEMARK OFFICE
CERTIFICATE OF CORRECTION

PATENT NO. : 7,204,857 B1
APPLICATION NO. : 09/622665
DATED : April 17, 2007
INVENTOR(S) : H. Andrean et al.

It is certified that error appears in the above-identified patent and that said Letters Patent is hereby corrected as shown below:

In claim 1, column 21, lines 63-66, "  " should read

-- 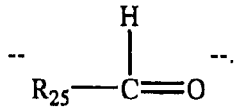 --.

In claim 9, column 24, line 26, "orthophthalalclehyde;" should read --orthophthalaldehyde;--.

In claim 9, column 24, lines 40-41, "4-methyithiobenzaldehyde;" should read --4-methylthiobenzaldehyde;--.

In claim 9, column 24, lines 55-56, "2,3-dihydroxy-4-methoxybeflzaldehyde;" should read --2,3-dihydroxy-4-methoxybenzaldehyde;--.

In claim 12, column 26, lines 10-11, "4-dimethylaminobanzaldehyde;" should read --4-dimethylaminobenzaldehyde;--.

In claim 17, column 27, line 20, "dehydes;" should read --aldehydes;--.

In claim 17, column 27, lines 30-33, " 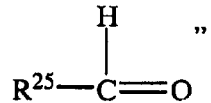 "

should read 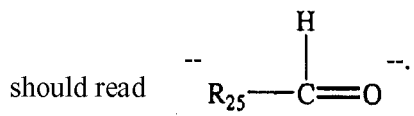

In claim 17, column 28, lines 1-2, "and the and the" should read --and the--.

UNITED STATES PATENT AND TRADEMARK OFFICE
CERTIFICATE OF CORRECTION

PATENT NO. : 7,204,857 B1
APPLICATION NO. : 09/622665
DATED : April 17, 2007
INVENTOR(S) : H. Andrean et al.

It is certified that error appears in the above-identified patent and that said Letters Patent is hereby corrected as shown below:

In claim 29, column 30, lines 10-11, "2-mono(2-hydroxyethoxy)benzaldehyde" should read --2-mono(2-hydroxyethoxy)benzaldehyde;--.

In claim 29, column 30, line 28, "4-diethylaminosalicylaldehyde" should read --4-diethylaminosalicylaldehyde;--.

In claim 51, column 33, lines 34-37, 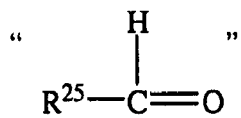 should read 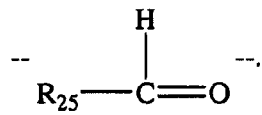.

In claim 51, column 33, line 52, "each from" should read --each chosen from--.

In claim 51, column 34, line 59, after "substituted; and" insert a paragraph break.

Signed and Sealed this

Twenty-ninth Day of January, 2008

JON W. DUDAS
*Director of the United States Patent and Trademark Office*